United States Patent
Wang et al.

(10) Patent No.: US 11,365,412 B2
(45) Date of Patent: Jun. 21, 2022

(54) PROMOTION OF CARDIOMYOCYTE PROLIFERATION AND REGENERATIVE TREATMENT OF THE HEART BY INHIBITION OF MICRORNA-128

(71) Applicant: University of Cincinnati, Cincinnati, OH (US)

(72) Inventors: Yigang Wang, Cincinnati, OH (US); Wei Huang, Cincinnati, OH (US)

(73) Assignee: University of Cincinnati, Cincinnati, OH (US)

(*) Notice: Subject to any disclaimer, the term of this patent is extended or adjusted under 35 U.S.C. 154(b) by 110 days.

(21) Appl. No.: 16/500,481

(22) PCT Filed: Apr. 5, 2018

(86) PCT No.: PCT/US2018/026168
§ 371 (c)(1),
(2) Date: Oct. 3, 2019

(87) PCT Pub. No.: WO2018/187523
PCT Pub. Date: Oct. 11, 2018

(65) Prior Publication Data
US 2021/0102202 A1    Apr. 8, 2021

Related U.S. Application Data

(60) Provisional application No. 62/481,793, filed on Apr. 5, 2017.

(51) Int. Cl.
| | | |
|---|---|---|
| *C07H 21/02* | (2006.01) | |
| *C07H 21/04* | (2006.01) | |
| *C12N 15/113* | (2010.01) | |
| *A61P 9/00* | (2006.01) | |
| *C12N 5/077* | (2010.01) | |

(52) U.S. Cl.
CPC ............ *C12N 15/113* (2013.01); *A61P 9/00* (2018.01); *C12N 5/0657* (2013.01); *C12N 2310/11* (2013.01); *C12N 2310/14* (2013.01); *C12N 2310/141* (2013.01); *C12N 2310/531* (2013.01); *C12N 2320/30* (2013.01); *C12N 2320/32* (2013.01)

(58) Field of Classification Search
CPC ............ C12N 15/113; C12N 2310/141; C12N 2310/11
See application file for complete search history.

(56) References Cited

U.S. PATENT DOCUMENTS

| | | | |
|---|---|---|---|
| 9,476,046 B2 * | 10/2016 | Naar | A61K 31/7105 |
| 2005/0214938 A1 | 9/2005 | Gold et al. | |
| 2012/0244136 A1 | 9/2012 | Robbins et al. | |
| 2013/0225665 A1 | 8/2013 | Wang et al. | |
| 2014/0221466 A1 | 8/2014 | Rudnicki et al. | |
| 2015/0232848 A1 | 8/2015 | Naar et al. | |
| 2016/0068863 A1 | 3/2016 | Aguirre et al. | |

OTHER PUBLICATIONS

Elbashir et al. (The EMBO Journal, vol. 20, No. 23, pp. 6877-6888, 2001).*
Yan et al. (J Cell Physiol, 2019, 234, 13452-13463).*
Zeng et al. (Molecular Medicine Reports, 14, 129-136, 2016).*
Ruixing et al. (Translational Research, 149, 3, 2007, 152-160).*
Scherr et al. (Nucleic Acids Research, 2007, 35, 22, e149, 1-9).*
Saraste et al. (European Journal of Clinical Investigation, 1999, 29, 380-386).*
Margaret S. Ebert et al., MicroRNA Sponges: Competitive Inhibitors of Small RNAs in Mammalian Cells; Nature Methods, Aug. 12, 2007, vol. 4, pp. 721-726.

* cited by examiner

*Primary Examiner* — Amy H Bowman
(74) *Attorney, Agent, or Firm* — Dinsmore & Shohl LLP

(57) ABSTRACT

Inhibitors of miRNA-128 capable of promoting cardiomyocyte mitotic cell proliferation and methods effective for regeneration of heart tissue.

10 Claims, 21 Drawing Sheets

Specification includes a Sequence Listing.

(expression miR-128)

(expression miR-128)

| | | |
|---|---|---|
| Mmu | 5'- UGCCUACUGGAAAUGCACUGUGG -3' | (SEQ ID NO: 31) |
| Rno | 5'- UGCCUACUGGAAAUGCACUGUGG -3' | (SEQ ID NO: 32) |
| Hsa | 5'- UGCCUACUGGAAAUGCACUGUGG -3' | (SEQ ID NO: 33) |
| miR-128 | 3'- UUUCUCGGCCAAGUGACACU -5' | (SEQ ID NO: 1) |

SEQUENCE LISTING

<160> NUMBER OF SEQ ID NOS: 33

<210> SEQ ID NO 1
<211> LENGTH: 21
<212> TYPE: RNA
<213> ORGANISM: Homo sapiens
<220> FEATURE:
<221> NAME/KEY: misc_feature
<223> OTHER INFORMATION: Human miRNA-128

<400> SEQUENCE: 1
ucacagugaa ccgguculu u                                              21

<210> SEQ ID NO 2
<211> LENGTH: 21
<212> TYPE: RNA
<213> ORGANISM: Artificial Sequence
<220> FEATURE:
<223> OTHER INFORMATION: Anti-miRNA-128 oligonucleotide

<400> SEQUENCE: 2
agugucacuu ggccagagaa a                                             21

<210> SEQ ID NO 3
<211> LENGTH: 21
<212> TYPE: RNA
<213> ORGANISM: Mus musculus
<220> FEATURE:
<221> NAME/KEY: misc_feature
<223> OTHER INFORMATION: Murine miRNA-128

<400> SEQUENCE: 3
ucacagugaa ccgguculu u                                              21

<210> SEQ ID NO 4
<211> LENGTH: 19
<212> TYPE: DNA
<213> ORGANISM: Artificial Sequence
<220> FEATURE:
<223> OTHER INFORMATION: PCR primer for 559 bp fragment from targeted
      allele

<400> SEQUENCE: 4
tgagccagac ctccatcgc                                                19

<210> SEQ ID NO 5
<211> LENGTH: 19
<212> TYPE: DNA
<213> ORGANISM: Artificial Sequence
<220> FEATURE:
<223> OTHER INFORMATION: PCR primer for 559 bp fragment from targeted
      allele

<400> SEQUENCE: 5
agctcggtac cattaatcg                                                19

```
<210> SEQ ID NO 6
<211> LENGTH: 21
<212> TYPE: DNA
<213> ORGANISM: Artificial Sequence
<220> FEATURE:
<223> OTHER INFORMATION: PCR primer for 413 bp fragment from wt allele

<400> SEQUENCE: 6
actccaaggc cacttatcac c                                              21

<210> SEQ ID NO 7
<211> LENGTH: 22
<212> TYPE: DNA
<213> ORGANISM: Artificial Sequence
<220> FEATURE:
<223> OTHER INFORMATION: PCR primer for 413 bp fragment from wt allele

<400> SEQUENCE: 7
attgttacca actgggacga ca                                             22

<210> SEQ ID NO 8
<211> LENGTH: 22
<212> TYPE: DNA
<213> ORGANISM: Artificial Sequence
<220> FEATURE:
<223> OTHER INFORMATION: PCR Primer for 234 bp fragment from wt allele
      and the 289 bp fragment from targeted allele

<400> SEQUENCE: 8
tcatagctgt acttactgga tg                                             22

<210> SEQ ID NO 9
<211> LENGTH: 20
<212> TYPE: DNA
<213> ORGANISM: Artificial Sequence
<220> FEATURE:
<223> OTHER INFORMATION: PCR Primer for 234 bp fragment from wt allele
      and the 289 bp fragement from targeted allele

<400> SEQUENCE: 9
cacttgggct tggaagatag                                                20

<210> SEQ ID NO 10
<211> LENGTH: 23
<212> TYPE: DNA
<213> ORGANISM: Artificial Sequence
<220> FEATURE:
<223> OTHER INFORMATION: PCR Primer for 483 bp fragment from wt allele
      and the 605 bp fragment from targeted allele

<400> SEQUENCE: 10
gccctaattt gatcatcaga acc                                            23

<210> SEQ ID NO 11
<211> LENGTH: 20
<212> TYPE: DNA
<213> ORGANISM: Artificial Sequence
<220> FEATURE:
<223> OTHER INFORMATION: PCR Primer for 483 bp fragment from wt allele
      and the 605 bp fragement from targeted allele

<400> SEQUENCE: 11
cattgttgta gccacacccc                                                20
```

<210> SEQ ID NO 12
<211> LENGTH: 20
<212> TYPE: DNA
<213> ORGANISM: Artificial Sequence
<220> FEATURE:
<223> OTHER INFORMATION: H3K27me3-p27 forward primer

<400> SEQUENCE: 12
gagatcctac ggtggaagcg                                       20

<210> SEQ ID NO 13
<211> LENGTH: 20
<212> TYPE: DNA
<213> ORGANISM: Artificial Sequence
<220> FEATURE:
<223> OTHER INFORMATION: H3K27me3-p27 reverse primer

<400> SEQUENCE: 13
cttagctggg gtgcggaatc                                       20

<210> SEQ ID NO 14
<211> LENGTH: 21
<212> TYPE: DNA
<213> ORGANISM: Artificial Sequence
<220> FEATURE:
<223> OTHER INFORMATION: miRNA-128 PCR Primer

<400> SEQUENCE: 14
cgtcacagtg aaccggtctc t                                     21

<210> SEQ ID NO 15
<211> LENGTH: 17
<212> TYPE: DNA
<213> ORGANISM: Artificial Sequence
<220> FEATURE:
<223> OTHER INFORMATION: U6 forward PCR primer

<400> SEQUENCE: 15
ctcgcttcgg cagcaca                                          17

<210> SEQ ID NO 16
<211> LENGTH: 20
<212> TYPE: DNA
<213> ORGANISM: Artificial Sequence
<220> FEATURE:
<223> OTHER INFORMATION: U6 reverse PCR primer

<400> SEQUENCE: 16
aacgcttcac gaatttgcgt                                       20

<210> SEQ ID NO 17
<211> LENGTH: 22
<212> TYPE: DNA
<213> ORGANISM: Artificial Sequence
<220> FEATURE:
<223> OTHER INFORMATION: Racgap1 forward PCR primer

<400> SEQUENCE: 17
cagatccagt gacaatgttc ca                                    22

<210> SEQ ID NO 18
<211> LENGTH: 22
<212> TYPE: DNA
<213> ORGANISM: Artificial Sequence
<220> FEATURE:
<223> OTHER INFORMATION: Racgap1 reverse PCR primer

```
<400> SEQUENCE: 18
tccaccatca tgaactgatt cc                                              22

<210> SEQ ID NO 19
<211> LENGTH: 21
<212> TYPE: DNA
<213> ORGANISM: Artificial Sequence
<220> FEATURE:
<223> OTHER INFORMATION: Nusap1 forward PCR primer

<400> SEQUENCE: 19
gaggaggaag aagcacaaga c                                               21

<210> SEQ ID NO 20
<211> LENGTH: 26
<212> TYPE: DNA
<213> ORGANISM: Artificial Sequence
<220> FEATURE:
<223> OTHER INFORMATION: Nusap1 reverse PCR primer

<400> SEQUENCE: 20
ctactatcag ttcctttcat ctccaa                                          26

<210> SEQ ID NO 21
<211> LENGTH: 20
<212> TYPE: DNA
<213> ORGANISM: Artificial Sequence
<220> FEATURE:
<223> OTHER INFORMATION: Myh10 forward PCR primer

<400> SEQUENCE: 21
gaattcgaga ggcagaacaa                                                 20

<210> SEQ ID NO 22
<211> LENGTH: 20
<212> TYPE: DNA
<213> ORGANISM: Artificial Sequence
<220> FEATURE:
<223> OTHER INFORMATION: Myh10 reverse PCR primer

<400> SEQUENCE: 22
aaggctcgct tggatttctc                                                 20

<210> SEQ ID NO 23
<211> LENGTH: 19
<212> TYPE: DNA
<213> ORGANISM: Artificial Sequence
<220> FEATURE:
<223> OTHER INFORMATION: Nppa forward PCR primer

<400> SEQUENCE: 23
ctgaggtgcc tccctggac                                                  19

<210> SEQ ID NO 24
<211> LENGTH: 21
<212> TYPE: DNA
<213> ORGANISM: Artificial Sequence
<220> FEATURE:
<223> OTHER INFORMATION: Nppa reverse PCR primer

<400> SEQUENCE: 24
actctgggct ccaatcctgt c                                               21
```

```
<210> SEQ ID NO 25
<211> LENGTH: 20
<212> TYPE: DNA
<213> ORGANISM: Artificial Sequence
<220> FEATURE:
<223> OTHER INFORMATION: Nppb forward PCR primer

<400> SEQUENCE: 25
aaggaccaag gcctcacaaa                                                     20

<210> SEQ ID NO 26
<211> LENGTH: 21
<212> TYPE: DNA
<213> ORGANISM: Artificial Sequence
<220> FEATURE:
<223> OTHER INFORMATION: Nppb reverse PCR primer

<400> SEQUENCE: 26
gccaggaggt cttcctacaa c                                                   21

<210> SEQ ID NO 27
<211> LENGTH: 20
<212> TYPE: DNA
<213> ORGANISM: Artificial Sequence
<220> FEATURE:
<223> OTHER INFORMATION: Myh6 forward PCR primer

<400> SEQUENCE: 27
ggacgcccag atggctgact                                                     20

<210> SEQ ID NO 28
<211> LENGTH: 23
<212> TYPE: DNA
<213> ORGANISM: Artificial Sequence
<220> FEATURE:
<223> OTHER INFORMATION: Myh6 reverse PCR primer

<400> SEQUENCE: 28
ccttgtcatc aggcacgaag cac                                                 23

<210> SEQ ID NO 29
<211> LENGTH: 23
<212> TYPE: DNA
<213> ORGANISM: Artificial Sequence
<220> FEATURE:
<223> OTHER INFORMATION: Myh7 forward PCR primer

<400> SEQUENCE: 29
gtttgtcaag gccaagatcg tgt                                                 23

<210> SEQ ID NO 30
<211> LENGTH: 20
<212> TYPE: DNA
<213> ORGANISM: Artificial Sequence
<220> FEATURE:
<223> OTHER INFORMATION: Myh7 reverse PCR primer

<400> SEQUENCE: 30
agcatggcca tgtcctcgat                                                     20

<210> SEQ ID NO 31
<211> LENGTH: 23
<212> TYPE: RNA
<213> ORGANISM: Mus musculus
```

```
<400> SEQUENCE: 31
ugccuacugg aaaugcacug ugg                                              23

<210> SEQ ID NO 32
<211> LENGTH: 23
<212> TYPE: RNA
<213> ORGANISM: Rattus norvegicus

<400> SEQUENCE: 32
ugccuacugg aaaugcacug ugg                                              23

<210> SEQ ID NO 33
<211> LENGTH: 23
<212> TYPE: RNA
<213> ORGANISM: Homo sapiens

<400> SEQUENCE: 33
ugccuacugg aaaugcacug ugg                                              23
```

PROMOTION OF CARDIOMYOCYTE PROLIFERATION AND REGENERATIVE TREATMENT OF THE HEART BY INHIBITION OF MICRORNA-128

CROSS REFERENCE TO RELATED APPLICATIONS

This application is a National Stage under § 371 of International Application No. PCT/US2018/026168, filed Apr. 5, 2018, which claims the benefit of U.S. Provisional Application No. 62/481,793, filed Apr. 5, 2017, each of which is incorporated herein by reference in its entirety.

GOVERNMENT RIGHTS

This invention was made with government support under HL130042, HL107957, and HL110740, awarded by National Institutes of Health. The government has certain rights in the invention.

TECHNICAL FIELD

The present disclosure relates to therapeutic regenerative medicine; namely inhibitors of miRNA-128 and methods for promoting proliferation of mitotic cardiomyocytes and regeneration of heart tissue for the treatment of cardiac disorders and diseases.

BACKGROUND

The adult human heart fails to replenish the massive loss of cardiomyocytes (CMs) caused by ischemia, which is the leading cause of death worldwide. Intensive research has recently focused on the development of regenerative therapies for ischemic heart disease. Current regenerative approaches are designed to repopulate lost CMs through transplantation of exogenous stem cells from various sources with committed cardiogenic potential. Unfortunately, the inability to differentiate efficiently, poor cell survival, immaturity of differentiated CM, and arrhythmia, have all hampered the application of stem cell-based therapy in clinical settings. Alternatively, cell-free approaches (such as stimulation of endogenous CM proliferation) have emerged as an attractive option for implementing myocardial regeneration.

There has been a longstanding dogma that adult mammalian CMs are incapable of cell division. Recent studies, however, have shown that the 1-day-old neonatal mouse can regenerate its heart through dedifferentiation and proliferation of pre-existing CMs (see, e.g. Porrello, E. R., et al. *Proc Nat'l Acad of Sci US* 110, 187-192 (2013), and Porrello, E. R., et al. *Science* 331, (2011) 1078-1080, the entire disclosures of which are incorporated herein), a phenomenon that is observed in lower vertebrates such as adult zebrafish and amphibians. Unlike the adult zebrafish, the capacity of the neonatal mouse heart to regenerate is diminished as early as 1 week after birth and remains limited throughout adulthood. Various hypotheses have been proposed to explain the different capacities of different species to undergo cardiac regeneration. Recent compelling evidence showing that CMs have the potential to divide implies there is a latent regenerative potential when endogenous CMs are triggered to proliferate. Most exciting is the recent finding of limited self-renewal of human adult CMs using measurements of carbon-14 ($^{14}C$) content by accelerator mass spectrometry (see, e.g. Bergmann, O., et al. *Cell* 161, 1566-1575 (2015), Bergmann, O., et al. *Circ Res* 110, e17-18, and Bergmann, O., et al. *Science* 324, 98-102 (2009)). Reactivation of CM proliferation, therefore, becomes even more appealing for the potential of heart regeneration. Whether, how and to what extent the endogenous proliferative ability of CM is sufficient to restore adult heart function, however, remains largely unknown.

MicroRNAs (miRNAs) constitute a class of small non-coding RNAs that bind to 3' untranslated region (3'UTR) of target mRNAs, resulting in the reduction of protein expression predominantly by destabilizing the target mRNAs and/or by inhibiting translation (Eulalio, A., et al. *Nature* (2012), Liu, N. & Olson, E. N. *Dev Cell* 18, 510-525 of CMs during MI (Qian, L., et al. *The Journal of experimental medicine* 208, 549-560 (2011), the entire disclosure of which is incorporated herein).

However, the miRNAs that regulate CM proliferation during homeostasis and injury are not fully understood. Dissecting the mechanisms by which adult CMs exit the cell cycle arrest is fundamental for therapeutic manipulation capable of stimulating endogenous CMs to proliferate in the adult myocardium. Although several CM cell cycle mediators have been identified, manipulation of the genes encoding these mediators has been insufficient for full recovery of heart function in response to injury.

Clearly, identification of target miRNA implicated in CM proliferation and provision of regenerative therapies based on modulating the target miRNA remain a compelling need in the art.

SUMMARY

Accordingly, the present invention provides embodiments directed miRNA-128 inhibitors capable of promoting CM mitotic cell proliferation and methods effective for regeneration of heart tissue.

The cardinal miRNA implicated in governing heart growth during homeostasis and following injury was identified by the inventors as miRNA-128. Using small RNA sequencing, miRNA-128 expression was shown to be upregulated during the postnatal switch to terminal differentiation, at a time when most cardiomyocytes exit the cell cycle. It was further found that cardiac-specific overexpression of miRNA-128 in a transgenic mouse model impairs CM proliferation and cardiac function in the neonate. Cardiac-specific deletion of miRNA-128, in contrast, extends the proliferation window of postnatal CMs, with no deleterious effects on cardiac function. Moreover, miRNA-128 deletion modulates the expression of cell cycle-related genes, in part through targeting the chromatin modifier Suz12. Deletion of miRNA-128 leads to enhanced enrichment of SUZ12 on the cyclin-dependent kinase inhibitor (CDKI) p27 promoter, with consequent repression of p27 expression and activation of Cyclin E and CDK2 of downstream positive cell cycle regulators that promote proliferation. Furthermore, deletion of miRNA-128 promotes re-entry of adult CMs into the cell cycle, thereby reducing the level of fibrosis, and attenuating cardiac dysfunction in response to MI. In aggregate, these results demonstrate that miRNA-128 is a critical regulator of endogenous CM proliferation, and provides a novel therapeutic target for heart repair.

Accordingly, one embodiment provides methods for treating a subject suffering from a cardiac disorder. The methods comprise the step of delivering a therapeutically effective amount of a miRNA-128 inhibitor to a myocardial region of the subject. The inhibitor can be delivered via transfection by a plasmid or vector comprising a genetic construct of the miRNA-128 inhibitor to the subject, or it may be delivered by enhanced transmission.

Another embodiment provides a miRNA-128 inhibitor selected from an antisense nucleic acid against miRNA-128. In some embodiments the anti-miRNA oligonucleotide comprises between 4 and 21 nucleotides. According to other embodiments the miRNA-128 inhibitor is a small molecule inhibitor. In still other embodiments regenerative mitotic CMs in which proliferative capacity has been restored by inhibition of miRNA-128 are administered to a myocardial region of the heart. The mitotic CMs may derive from the subject.

Embodiments directed to pharmaceutical compositions comprising at least one miRNA-128 inhibitor or at least one plasmid or vector engineered to transfect a cardiomyocyte with at least one miRNA-128 inhibitor, and a pharmaceutically acceptable vehicle aspect are also provided.

Yet another embodiment is directed to methods for promoting proliferation of cardiomyocyte cells. The methods comprise adding an effective amount of a miRNA-128 inhibitor to a culture medium comprising the cardiomyocyte cells, and observing proliferating regenerative cardiomyocyte cells. Compositions of regenerative cardiomyocyte cells may be directly administered to a myocardial region of a subject that would benefit from regenerative therapy.

In some embodiments, pharmaceutical compositions of the invention may be administered directly to the myocardial region in a subject in need of regenerative therapy, for example by catheter-based injection. Direct injection may be guided by imaging technology, for example angiographic computed tomography imagine or real time magnetic resonance.

These and other embodiments and aspects of the invention will be more fully explained and clarified by reference to the Figures and detailed description, below.

DETAILED DESCRIPTION

Figure 1A:
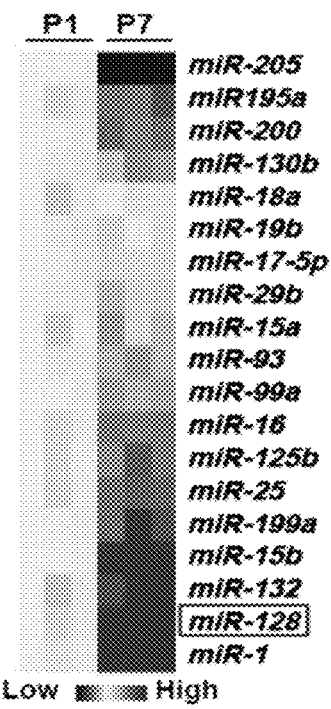
FIG. 1A) The level of miRNA-128 increases as the heart progresses from neonatal to adult, sets forth customer qPCR array of miRNA expression in wild type (WT) mouse hearts at postnatal day 1 (P1) and P7.

Embodiments of the invention provide a novel therapeutic target for treatments that activate endogenous cardiac proliferation and cardiac function recovery after heart damage.

The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Involvement of microRNAs (miRNA or miR) has been invoked as one mechanism underlying regulation of cell proliferation. miRNAs are an abundant class of small (approximately 22 nucleotides) endogenous non-coding RNAs that direct post-transcriptional regulation of gene expression. Metazoan miRNAs regulate a wide range of biological processes, including developmental timing, apoptosis, differentiation, cell proliferation and metabolism. Evidence is accumulating that dysregulation of individual or entire families of miRNA is associated with the pathogenesis of human diseases, such as cancer, CNS disorders, viral infections, cardiovascular and metabolic diseases. Identification and experimental validation of miRNA targets is a key prerequisite for uncovering the widespread biological roles of miRNAs and miRNA-mediated gene regulatory networks.

The present investigators surprisingly discovered that inhibition of miRNA-128 in vivo promotes cardiac regeneration by activating CM proliferation, and, as illustrated by the Examples set forth below, have empirically demonstrated: 1) miRNA-128 expression is upregulated after birth and this upregulation is associated with the cell cycle exit of CMs during postnatal development; 2) overexpression of miRNA-128 expression leads to premature cell cycle arrest and cardiac hypertrophy; 3) miRNA-128 regulates some cell cycle genes in vivo, including p27; 4) overexpression of miRNA-128 inhibits CM proliferation and neonatal heart regeneration; and 5) inhibition of miRNA-128 prolongs the postnatal CM proliferation window and activates endogenous cardiac regeneration capacity in adult heart.

It was previously known that as a neuronal-enriched miRNA, miRNA-128 is associated with central nervous system development and is downregulated in gliomas. Downregulation of miRNA-128 accelerates glioma-initiating neural stem cell proliferation and contributes to the development of gliomas. According to the present investigations, miRNA-128 is revealed as a negative regulator of the CM cell cycle, in which deletion of miRNA-128 prolongs the postnatal CM proliferation window, as evidenced by pronounced sarcomere disassembly and expression of markers of cycling cells such as pH3, Ki67, and EdU incorporation. Normal growth in the developing heart requires a proper balance between cycling cells and cells that exit the cycle. Disturbance in this balance can be associated with hypertrophy. Consistently, the transgenic mice with miRNA-128 overexpression displayed cardiac hypertrophy and cardiac dysfunction due to the premature cell cycle exit. Thus, activation miRNA-128 may participate in pathogenesis of congenital heart disease involving abnormalities of myocardial growth.

Cell cycle exit in CMs is accompanied by downregulation of positive cell cycle regulators and upregulation of CDKIs. Among the target genes regulated by miRNA-128, is Suz12, whose expression was significantly lower in adult hearts.

This finding suggests that Suz12 plays a primary role in cardiomyocyte cell cycle regulation in the later stages of heart development and in neonatal cell cycle withdrawal. Results of the present studies demonstrate that knockdown of SUZ12 resulted in a reduction of CM proliferation, which is consistent with its reported function of catalyzing the trimethylation of H3K27 to mediate gene silencing and playing a fundamental role in mouse development. Accompanied with the upregulation of SUZ12, downregulation of negative cell cycle regulators (such as p27) and upregulation of downstream positive cell cycle regulators such as Cyclin E and CDK2 was observed in the miRNA-128 deficient heart.

P27, as a major member of CIP/KIP CDKI family, has been implicated in CM cell cycle arrest, and deletion of P27 promotes CM entry into S-phase. P27 can also negatively modulate the activity of Cyclin E dependent kinase, a requirement for entry of cells into S phase. In keeping with these observations, the present investigations suggest that elimination of miRNA-128 activates cell cycle-related genes, in part through SUZ12-regulated histone modification, thereby promoting CM proliferation.

Since SUZ12 is chromatin associated protein that is broadly distributed, it is likely that it regulates other genes involved in CM proliferation. Thus, it would be informative to perform ChIP-Seq and RNA-Seq to systemically identify SUZ12 target genes to better understand how SUZ12 modulates the activity of EZH2, the enrichment of H3K27me3 and transcriptional output.

Using a gain-of-function genetic approach in neonatal cardiac injury model, the investigators found that miRNA-128 overexpression inhibited CM proliferation and neonatal heart regeneration. These findings highlight the involvement of miRNA-128 in the molecular pathway that arrests CM proliferation and cardiac regeneration after birth.

To assess the potential therapeutic benefit of miRNA-128 inhibition in the heart after cardiac damage, a cardiac-specific, tamoxifen-inducible miRNA-128 knockout mouse model was developed. The effect of miRNA-128 deletion on the cell cycle was evident in adult stages, when adult CMs become profoundly differentiated and quiescent and their ability to divide is quite limited. Using genetic lineage tracing, the results provide proof that preexisting CMs rather than progenitor cells are, in fact, the target cells that respond to miRNA-128 deletion during regeneration after cardiac damage. These adult CMs lacking miRNA-128 can be 'rejuvenated' to an immature stage that allows them to dedifferentiate and enter a proliferative state, an endogenous program for natural heart regeneration occurred in the zebrafish and neonatal mice in response to injury.

Of particular note, the changes in cellular capabilities induced by loss of miRNA-128 results in increased cellular plasticity that allows significant anatomical and functional capacity upon injury, but does not impair heart function under normal conditions.

Embodiments of the invention provide methods for activating endogenous cardiomyocyte proliferation by targeting miRNA-128, and treatment methods of inducing myocardial regeneration. Other embodiments are directed to therapeutic agents and compositions effective for inducing CM proliferation and heart tissue regeneration.

One embodiment is directed to methods for treating a subject suffering from a cardiac disorder. Contemplated cardiac disorders include any disease or condition of the heart benefited by proliferation of cardiomyocytes and regeneration of heart tissue. Non-limiting examples include ischemic cardiomyopathy, including but not limited to myocardial infarction; non-ischemic cardiomyopathy, including but not limited to hypertrophic cardiomyopathy, dilated cardiomyopathy and diabetic cardiomyopathy; valvular heart disease; heart failure; myocardial stunning, intermittent claudication; tachycardia; stroke; hypotension; embolism; thromboembolism (blood clot); sickle cell disease; and combinations thereof. The methods comprise delivering a therapeutically effective amount of a miRNA-128 inhibitor to a myocardial region of the subject.

Embodiments of the invention provide inhibitors of human miRNA-128 (miRNA-128 *Homo sapiens* UCACAGUGAACCGGUCUCUUU (SEQ ID NO: 1)) and the identical murine miRNA-128 (*Mus musculus* UCACAGUGAACCGGUCUCUUU) (SEQ ID NO: 3). The present oligonucleotide inhibitor sequesters and/or binds to the miRNA-128 sequence and blocks its activity. In specific embodiments the anti-miRNA oligonucleotide comprises at least 4, at least 5, at least 6, at least 7 or at least 8 nucleotides of the sequence AGUGUCACUUGGCCAGAGAAA (SEQ ID NO: 2).

Additional miRNA-128 inhibitor embodiments include, but are not limited to: 1). miRNA sponges. DNA vectors that express "microRNA sponges" that are competitive inhibitors of miRNAs have been disclosed. Adenovirus-associated vectors (AAV)-based constructs are currently being used in several clinical trials for gene therapy, and the safety profiles are encouraging (see, e.g. Aalbers et al. "Advancements in adeno-associated viral gene therapy approaches: exploring a new horizon" (2011) F1000 Med Rep 3: 17, and Ebert, M. S. et al. (2007) Nat Methods, 4, 721-726, the entire disclosures of which are incorporated herein by this reference). AAV as gene therapy vector can infect both dividing and quiescent cells with persistent expression. An additional attractive feature of AAV is not integrating into the genome of the host cell. Therefore, transcripts expressed from plasmids possessing multiple tandem binding sites for targeted miRNA-128 can be constructed into AAV;

2). Chemically modified miRNA-targeting antisense oligonucleotides. A nucleic acid sequence complementary to miRNA-128 can be conjugated to fatty acids, lipids, saccharides, peptides, proteins, locked nucleotide analogues (LNAs), morpholino oligomers or other bioactive molecules to enhance the bio-stability. Chemically modified single-stranded oligonucleotides such as 2'-O-methyl (2'-OMe) RNA (Hutvagner, G et al. (2004) PLoS Biol. 2, E98; Meister, G et al. (2004) Rna, 10, 544-550, incorporated herein by reference), locked nucleic acid (LNA), and "antagomirs" (Oron, U. A. et al. (2006) Gene, 372, 137-141: Krutzfeldt, J. et al. (2005) Nature, 438, 685-689, incorporated herein by reference) are known. These reagents are chemically synthesized to have complementarity towards mature miRNAs and are designed to be introduced into cells by transfection. They are resistant to cellular nucleases, and may function as substrates not cleaved by RISC.

3). Small-molecule inhibitors. Small molecule inhibitors have been designed to target at least the three steps of the miRNA transcription, assembly, and function. Additionally, these miRNA-128 inhibitors can be encapsulated into a lipid-based formulation or nanoparticles that enhance tissue-specific delivery.

Recent interest in the therapeutic potential for various microRNA species has spurred substantial development in the synthesis/discovery of expression modulators, including inhibitors. Although generation of antimiRNAs for specific miRNA inhibition is routine, optimization of the oligonucleotides for increased binding affinity, improved nuclease resistance and in vivo delivery is required. According to specific embodiments, the miRNA-128 inhibitor comprises an oligonucleotide comprising an antisense nucleic acid against miRNA-128, wherein the oligonucleotide may be chemically modified or unmodified. Anti-miRNA oligonucleotides (AMOs) appear to work primarily through a steric blocking mechanism of action. According to very specific embodiments the inhibitor compound is a synthetic reverse complement that tightly binds and inactivates miRNA-128. A variety of chemical modifications can be used to improve the performance and potency of AMOs. In general, modifications that confer nuclease stability and increase binding affinity improve AMO performance. Chemical modifications and/or certain structural features of the AMO may also facilitate invasion into the miRNA-induced silencing complex. In particular, it is essential that the AMO binds with high affinity to the miRNA 'seed region', which spans bases 2-8 from the 5'-end of the miRNA.

One embodiment provides an isolated nucleic acid molecule comprising (a) a nucleotide sequence as shown in SEQ ID NO: 1, or a precursor of SEQ ID NO: 1 and/or (b) a nucleotide sequence which is the complement of (a), and/or (c) a nucleotide sequence which has an identity of at least 80% to a sequence of (a) or (b), and/or (d) a nucleotide sequence which hybridizes under stringent conditions to a sequence of (a), (b) and/or (c) wherein said isolated nucleic acid molecule comprises at least one modified building block, wherein the modified building block is selected from the group consisting of nucleobase-modified building blocks, sugar-modified building blocks, backbone-modified building blocks and combinations thereof. Such methods are set forth in detail in Stenvang et al. "Inhibition of microRNA function by antimiR oligonucleotides" Silence 2012; 3: 1, the entire disclosure of which is incorporated herein in its entirety by this reference.

Modified nucleotide building blocks may be selected from nucleobase-, sugar- and backbone-modified building blocks and combinations thereof, i.e. building blocks having several modifications, e.g. a sugar and a backbone modification. Nucleobase-modified building blocks comprise a non-standard nucleobase instead of a standard nucleobase (e.g. adenine, guanine, cytosine, thymine or uracil) such as a uracil or cytosines modified at the 5-position, e.g. 5-methylcytosine, 5-(2-amino)propyluracil, 5-bromouracil, adenines or guanines modified at the 8-position, e.g. 8-bromoguanine, deazapurine nucleobases, e.g. 7-deaza-adenine and O- or N-alkylated nucleobases, e.g. N6 alkyl-adenine.

In some embodiments, the modified nucleotide building blocks encompass sugar-modified building blocks, particularly sugar-modified ribonucleotide building blocks, wherein the 2'OH group is replaced by a group selected from H, OR, R, halo, SH, SR, NH, NHR, $NR_2$ or CN, wherein R is $C_1$-$C_6$ alkyl, $C_2$-$C_6$ alkenyl or $C_2$-$C_6$ alkynyl and halo is F, Cl, Br or I. Further preferred sugar-modified nucleotides are selected from LNA or morpholino nucleotides. In certain aspects of the backbone-modified building blocks, the phosphoester group connecting to adjacent building blocks is replaced by a modified group, e.g. by replacing one or more O atoms of the phosphoester group by S, Se, NR or $CR_2$, wherein R is as defined above. It should be noted that the above modifications may be combined.

The nucleic acid molecule may be conjugated to heterologous molecules, e.g. non-nucleic acid molecules such as fatty acids, lipids, saccharides, peptides, proteins, antibodies, nanoparticles, peptide nucleic acids (PNAs), locked nucleotide analogues (LNAs).

In very specific embodiments, sequence (c) has a sufficient sequence complementarity to miRNA-128 and/or a precursor thereof in order to mediate target-specific inhibition, e.g. by forming a double-stranded hybrid with the target. Preferably, the sequence has a complementarity of at least 50%, at least 70%, at least 80%, at least 85%, at least 90%, at least 95% or up to 100% in the portion which corresponds to the target.

The isolated nucleic acid molecule may be single-stranded or double-stranded. In very specific embodiments, the isolated nucleic acid molecule is a miRNA molecule or an analog thereof having a length of from 18-25 nucleotides, or a miRNA precursor molecule having a length of 50-120 nucleotides or a DNA molecule coding therefor. Even more specifically, the isolated nucleic acid molecule is an RNA molecule.

According to some embodiments, the isolated nucleic acid molecule is suitable for the diagnosis, treatment or prevention of a disorder involving cardiomyocyte death, including but not limited to ischemic cardiomyopathy (including but not limited to myocardial infarction), non-ischemic cardiomyopathy (including but not limited to hypertrophic cardiomyopathy), dilated cardiomyopathy, diabetic cardiomyopathy, valvular heart disease, heart failure, myocardial stunning, stroke, hypotension, embolism, thromboembolism (blood clot), and combinations thereof.

Embodiments directed to pharmaceutical compositions comprising an inhibitor of miRNA-128 are also contemplated. In specific embodiments the inhibitor is an isolated nucleic acid molecule comprising at least one modified building block and has sufficient complementarity to miRNA-128 to form a hybrid under physiological conditions. The inhibitor may be a single-stranded or double-stranded nucleic acid molecule. In very specific embodiments the inhibitor is an RNA molecule comprising at least one modified building block selected from the group consisting of nucleobase-modified building blocks, sugar-modified building blocks, backbone-modified building blocks and combinations thereof.

In one embodiment, the inhibitor may be an siRNA, that is, a double-stranded RNA molecule capable of RNA interference which is directed against a transcript comprising miRNA-128 or precursors thereof. In specific embodiments the siRNA molecule is a double-stranded RNA molecule, wherein each strand has a length of 15-30, preferably 19-25 nucleotides, which optionally has at least one 3'-overhang having a length of 1-5 or 1-3 nucleotides. Typical siRNA molecules are for example described in WO 02/044321, the content of which is incorporated herein by reference.

In another embodiment, the nucleic acid inhibitor is an antagomir, which is a single-stranded RNA molecule having a length of from 10 to 30 nucleotides, preferably from 12 to 25 nucleotides and even more preferably from 15 to 22 nucleotides. The antagomir may be perfectly complementary to its specific miRNA target with mispairing at the cleavage side of Ago2 and/or the presence of at least one modified building block to inhibit Ago2 cleavage. Antagomirs are for example disclosed in Kriltzfeldt et al., 2005, Czech, 2006 or Fiedler et al., 2011, the contents of which are incorporated herein by reference. Preferred antagomirs are cholesterol-conjugated, LNA-conjugated or FMOE-conjugated. In a very specific embodiment the antagomirs are directed against miRNA-128.

The nucleic acid inhibitors of the invention may be prepared by conventional methods, e.g. by chemical synthesis methods usually involving solid-phase synthesis according to standard protocols. The inhibitors can also be prepared by enzymatic transcription from synthetic DNA templates or from DNA plasmids, e.g. isolated from recombinant bacteria. Typically, phage RNA polymerases are used, such as T7, T3 or SP6 RNA polymerase. Several commercial sources exist for specific miRNA inhibitors. Although human data is scarce, several companies have developed, for example, anti-miRNA-122-based therapeutics for the treatment of HCV infections (See, e.g. Hildebrandt-Eriksen et al. "A unique therapy for HCV inhibits microRNA-122 in humans and results in HCV RNA suppression in chronically infected chimpanzees results from primate and first-in-human studies" Hepatology. 2009; 50:LB19, and Landford R E et al. "Therapeutic silencing of microRNA-122 in primates with chronic hepatitis C virus infection" *Science* 2010; 327:198-201, and Janssen et al. "Treatment of HCV infection by targeting microRNA" *N Engl J Med.* 2013; 368:1685-1694, the entire disclosures of which are incorporated herein by this reference.). Data from the reported trials has shown that short-term use of inhibitor of miRNA-122 in patients with chronic HCV genotype 1 infection is safe and well tolerated and provides long-lasting antiviral activity without evidence of viral resistance. The results of these studies demonstrate that pharmacological modulation of miRNA activity is a feasible therapeutic strategy in human patients.

Thus, dozens of miRNA species inhibitors have recently been developed and optimized and any particularly desired inhibitor species are readily synthesized as either vector-based expression clones or as synthetic oligonucleotides. Vector-based expression clones are typically available in lentiviral and non-viral vectors. MiRNA inhibitor clones bind specifically to their target miRNA's allowing transient as well as stable suppression of the target gene. Selection of promoter allows constitutive expression of inhibitors in all types of mammalian cells. MiRNA-128 inhibitors are commercially available; for example, from Genecopoeia (www.genecopoeia.com/product/mirna-inhibitor) and Sigma Aldrich (see www.signaaldrich.com/life-science/functional-genomics-and-mai/mirna/mirna-inhibitors-introduction).

According to some embodiments, miRNA-128 inhibitor may be administered as a pharmaceutical composition comprising a pharmacologically acceptable carrier and diluent. Delivery of anti-miRNA-128 oligonucleotide is via transfection or assisted uptake. In some embodiments the oligonucleotide is unconjugated or 3'-cholesterol modified. Administration methods potentially include injection, including intravenous and intraperitoneal injection, viral transfer, application of liposomes, and systemic/oral intake. The following references provide guidance on effective delivery/administration of anti-miRNA oligonucleotides and the disclosures of all are incorporated herein by reference, Broderick J A et al. "MicroRNA therapeutics" *Gene Ther.* 2011; 18:1104-1110; Rooij E., et al. "The art of microRNA research" *Circ Res.* 2011; 108:219-234; and Stenvang J. et al. "MicroRNAs as targets for antisense-based therapeutics" *Expert Opin Biol Ther.* 2008; 8:59-81.

In one aspect, the step of delivering comprises administering a plasmid/vector comprising a genetic construct of the miRNA-128 inhibitor to the subject. According to other aspects, the step of delivering comprises systemic administration of a vehicle comprising the inhibitor, said vehicle designed for targeted delivery to a myocardial region of the subject. Targeted delivery, for example, may be achieved by designing a liposome or micro/nanoparticle to specifically target heart tissue and release contents comprising miRNA inhibitor into a myocardial region of the subject.

Validation of myocardial viability and wall-motion assessment by noninvasive tests (e.g. NOGA mapping system, single photon emission computed tomography (SPECT), PET, echocardiography, MRI and cardiac nuclear medicine imaging) may be necessary to assist target delivery of miRNA-128 inhibiting gene constructs or drugs in the myocardium. With delineation of the myocardial viability by noninvasive methods (e.g. NOGA mapping system) catheter-based direct intramyocardial injection of cells or gene constructs reduces the likelihood of systemic toxicity of the injected substance, resulting in minimal washout, limited exposure of nontarget organs, and precise localization to ischemic and peri-ischemic myocardial regions in patients with chronic myocardial ischemia.

Systemic administration includes intravenous or oral. Delivery may also be intraperitoneal, such as directly into a myocardial region of the subject. According to specific embodiments, the step of delivering comprises directly administering a plasmid or viral vector engineered to transfect cardiomyocyte cells located in the myocardial region of the subject with the inhibitor. In more specific embodiments, directly administering comprises injecting or pressure injecting a composition comprising microRNA inhibitor directly into a myocardial region of a subject. In very specific embodiments directly injecting is via catheter-based direct intramyocardial injection to an ischemic or peri-ischemic myocardial region of the subject.

In some embodiments, validation of myocardial viability and wall-motion assessment by noninvasive tests (e.g. NOGA mapping system, single photon emission computed tomography (SPECT), PET, echocardiography, MRI and cardiac nuclear medicine imaging) is employed to assist targeted delivery of gene constructs or drugs in the myocardium. With delineation of the myocardial viability by noninvasive methods (NOGA mapping system; see, e.g. Gyöngyösi M. et al. "Diagnostic and prognostic value of 3D NOGA mapping in ischemic heart disease" *Nat Rev Cardiol.* 2011; 17; 8(7):393-404 and Kastrup J. et al. "Direct intramyocardial plasmid vascular endothelial growth factor-A165 gene therapy in patients with stable severe angina pectoris: A randomized double-blind placebo-controlled study: the Euroinject One trial" *J Am Coll Cardiol.* 2005 5; 45(7):982-8, the entire disclosures of which are incorporated herein by this reference), catheter-based direct intramyocardial injection of cells or gene constructs reduces the likelihood of systemic toxicity of the injected substance, resulting in minimal washout, limited exposure of nontarget organs, and precise localization to ischemic and peri-ischemic myocardial regions in patients with chronic myocardial ischemia.

It is widely reported that decreasing expression of miRNA-128 may be associated with increasing susceptibility to certain cancers, to proliferation of tumor cells in extant tumors, and to decreased responsiveness to cancer therapeutics. In particular, inhibition of miRNA-128 is associated with certain proliferative disorders of the brain. Therefore it is desirable that the therapeutic effects of treatment with miRNA inhibitor be localized and transient. In very specific embodiments the desired therapeutic inhibition of microRNA expression in cardiomyocytes lasts for a duration sufficient to regenerate cardiac tissue to normal functioning and to avoid deleterious effects.

The following Examples are provided to evidence, illustrate and clarify certain embodiments and aspects of the invention and should not be construed as limiting the scope of the invention as defined by the appended claims.

EXAMPLES

The following examples collectively demonstrate that the level of cardiac miRNA-128 is lower in neonates than in adults, and is further reduced during neonatal heart regeneration. Furthermore, cardiac-specific overexpression of miRNA-128 in early postnatal mice suppressed CM proliferation and caused impaired cardiac function. Conversely, knockout of miRNA-128 reactivated CM proliferation and cardiac regeneration in adult mouse, in part through modulation of cell cycle genes by targeting Suz12 in the heart.

Example 1

This Example Demonstrates that the Level of miRNA-128 Increases as the Heart Progresses from Neonate to Adult.

Figure 1B:
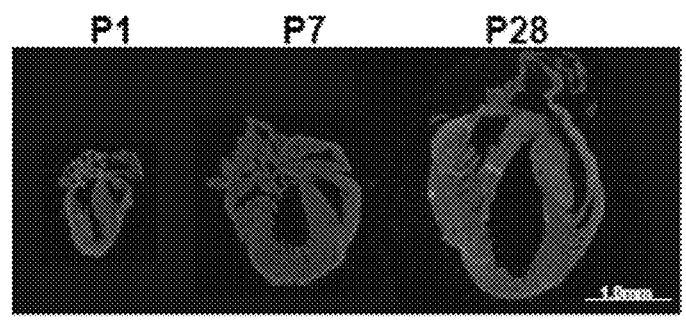
FIG. 1B) stereomicroscopic morphology of wild type mouse (WT) hearts at P1, P7, and P28.
Figure 1C:
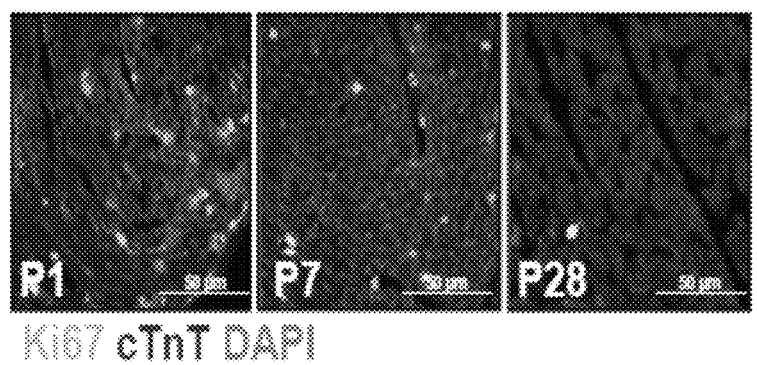
FIG. 1C and FIG. 1D) evaluation of cardiomyocyte (CM) cell-cycle activity using Ki67 (cell cycling marker) immunostaining.
Figure 1D:
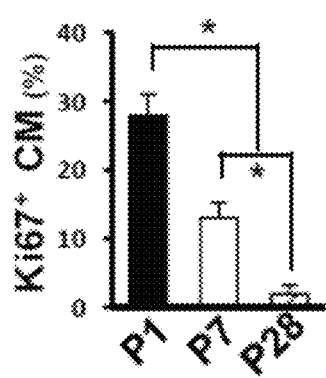
Figure 1E:
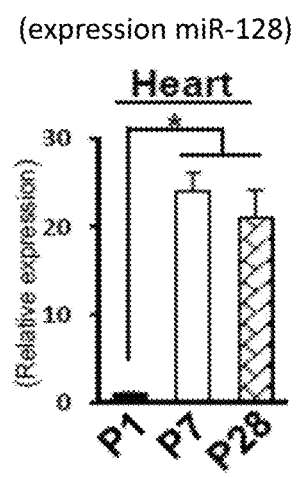
FIG. 1E) qPCR data of miRNA-128 expression of P1, P7 and P28 heart.
Figure 1F:
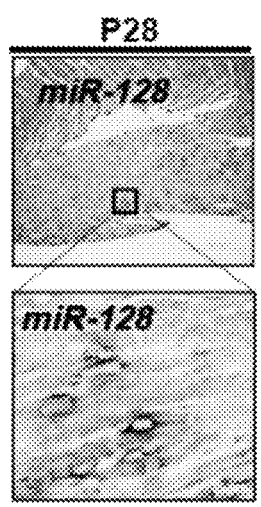
FIG. 1F) Representative image of adult mouse (P28) ventricular cross-sections analyzed by in situ hybridization using digoxigenin-labeled miRNA-128 probe.
Figure 1G:
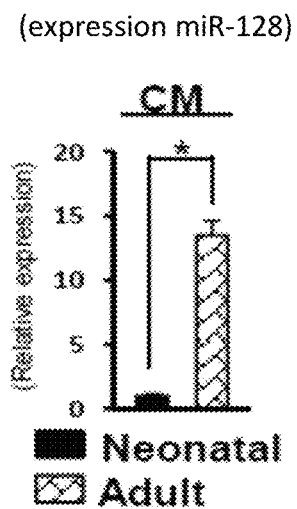
FIG. 1G) qPCR data of miRNA-128 expression in neonatal and adult CM. Statistical significance was calculated using ANOVA in D-E and Student's t-test in G. Data are means±SEM (n=5). *P<0.05.

Small RNA sequencing in mouse cardiac ventricles was performed on postnatal days 1, 7, and 28 (P1, P7, and P28) to identify potential miRNAs involved in the regulation of postnatal heart. One of the most robustly upregulated miRNAs during this period was miRNA-128 (FIG. 1A). As previously reported, miRNA-128 is predominantly expressed in brain tissue; but is also expressed in the heart (FIG. 1B). Its expression in adult myocardium was further confirmed by in situ hybridization (ISH) (FIG. 1C). To investigate the role of miRNA-128 in cell cycle withdrawal during heart development, mouse hearts were harvested and sectioned at P1, P7, and P28 as shown in FIG. 1A. As neonates progress to adulthood (from P1 to P28), CMs underwent a maturation process characterized by suppression of cell proliferation as evidenced by decreased numbers of Ki67$^+$ CMs (FIGS. 1C and D). To adapt to the increase in size of an organism, cardiac mass increases (FIG. 1B) primarily by an increase in CM size rather than in number (FIG. 1E and FIG. 1F). The level of miRNA-128 was found to be significantly elevated in P7 and P28 hearts compared with P1 hearts (FIG. 1G). In order to examine whether the postnatal upregulation of miRNA-128 occurs specifically in the CMs, CMs in neonatal (P1) and adult (P28) hearts were isolated and significantly higher levels of miRNA-128 were found in P28 CMs when compared to P1 CMs (FIG. 1H). Moreover, miRNA-128 in CMs was significantly higher than that of non-CMs (i.e. cardiac fibroblasts, CF) (FIG. 1I). These data indicate a potential critical role played by miRNA-128 in regulating CM proliferation.

Example 2

This Example Demonstrates that Overexpression of miRNA-128 Impairs Cardiac Homeostasis.

Figure 2A:
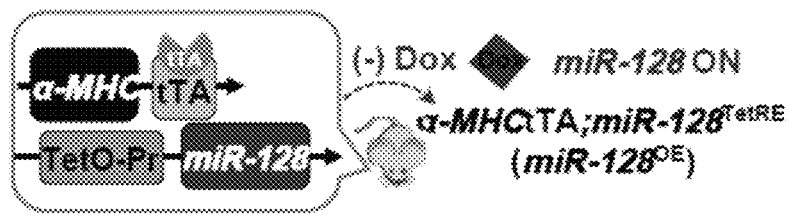
FIG. 2A) Overexpression of miRNA-128 impairs cardiac homeostasis, generation of CM-specific miRNA-128 overexpression mice.
Figure 2B:
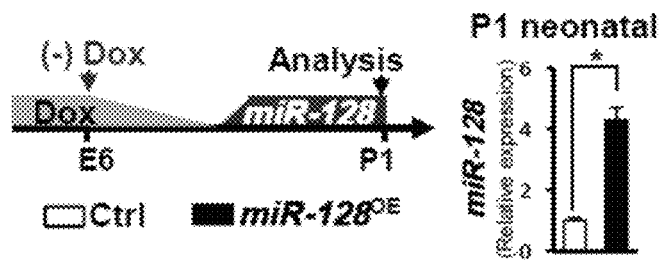
FIG. 2B) experimental design for CM-specific overexpression of miRNA-128 at P1(left), qPCR analysis of miRNA-128 expression in control miRNA-128$^{TetRE}$ mice (Ctrl) and miRNA-128 over expression ice (niR-128$^{OE}$)
Figure 2C:
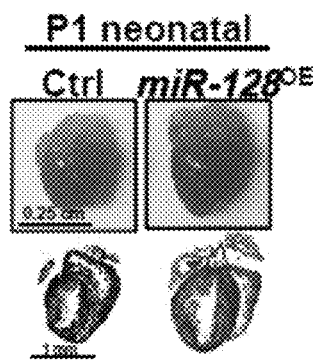
FIG. 2C) gross morphology of P1 hearts (upper), representative image of Masson Trichrome staining on hearts at P1(bottom)
Figure 2D:
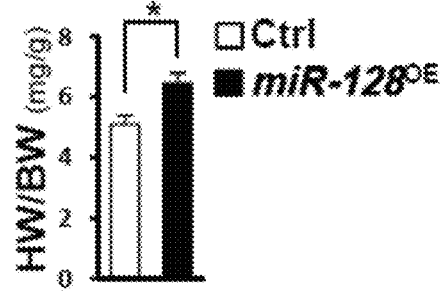
FIG. 2D) heart weight (HB) to body weight (BW) ratio in P1 mice (n=8)
Figure 2E:
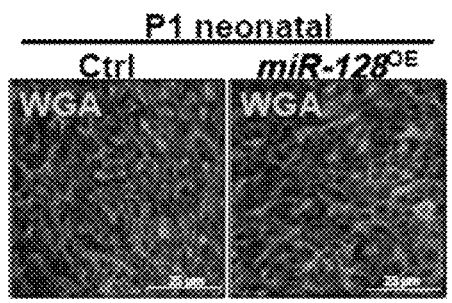
FIG. 2E) wheat germ agglutinin (WGA) staining of hearts (n=8)
Figure 2F:
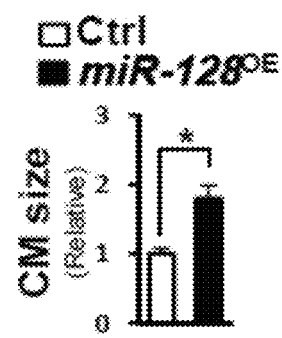
FIG. 2F) quantification of CM size as shown in WGA staining.
Figure 2G:
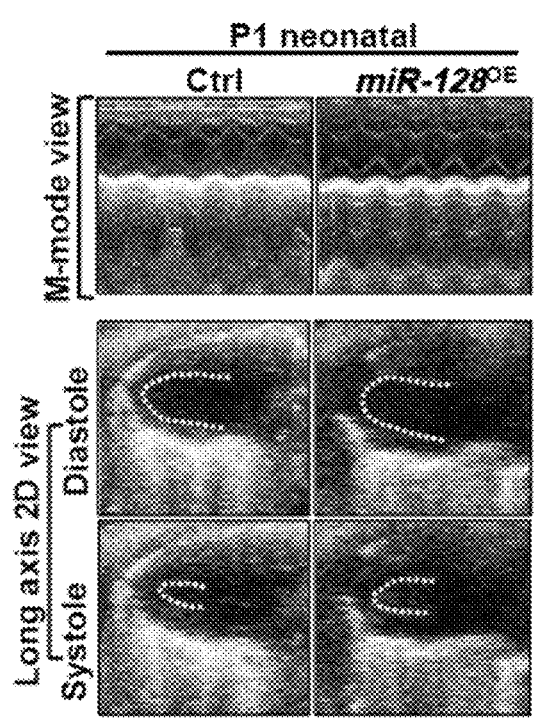
FIG. 2G) heart function analyzed by echocardiography in P1 mice, as measured by left ventricular ejection fraction (EF %) (n=6)
Figure 2H:
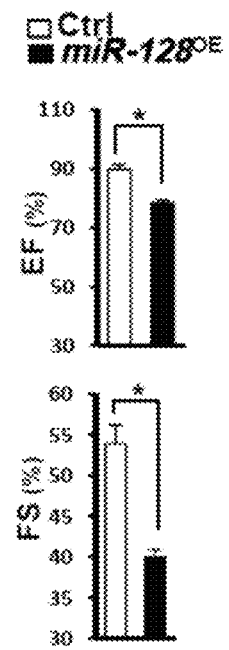
FIG. 2I) evaluation of CM cell-cycle activity by Ki67 immunostaining.
FIG. 2J) quantification data of Ki67$^+$ CM number in P1 heart (n=6). Statistical significance was calculated using Student's t-test. Data are means±SEM. *P<0.05.

To elucidate the specific function of miRNA-128 in the heart, a mouse model was developed in which miRNA-128 expression is under control of α-myosin heavy chain (α-MHC) promoter that is under temporal regulation by doxycycline (Dox). This "Tet-off" transgenic mouse (α-MHC-tTA; miRNA-128$^{TetRE}$) was produced by crossing α-MHC-tTA mice with miRNA-128$^{TetRE}$ mice (FIG. 2A). In α-MHC-tTA; miRNA-128$^{TetRE}$ mice, the TetRE portion of tTA binds to the TetO sequences after Dox withdrawal, and subsequently induces the CM-specific overexpression of miRNA-128 (designated as miRNA-128$^{OE}$ mice) in defined temporal windows (FIG. 2A and FIG. 2B). In general, induced transgene expression begins during the second week of Dox withdrawal due to the slow clearance of Dox from tissues. Withdrawal of Dox from miRNA-128$^{OE}$ fetuses starting at embryonic day 6 (E6) resulted in significant induction of miRNA-128 in miRNA-128$^{OE}$ hearts at the P1 neonatal stage as determined by qPCR (FIG. 2B). At P1, the explanted hearts from miRNA-128$^{OE}$ mice were markedly enlarged (FIG. 2C) compared with hearts from miRNA-128 TetRE mice (Control mice, designated as Ctrl). The higher heart-to-body weight ratios (HW/BW) of miRNA-128$^{OE}$ mice relative to Ctrl showed a progressive increase of heart mass (FIG. 2D). Morphologically, CM size was measured by staining with Wheat Germ Agglutinin (WGA) and showed that miRNA-128$^{OE}$ CMs were significantly larger than Ctrl CMs (FIG. 2E-F), implying the development of cardiac hypertrophy. Then, cardiac functions in Ctrl and miRNA-128$^{OE}$ mice were evaluated at P1 by echocardiography (FIG. 2G). Left ventricular (LV) ejection fraction (EF) and fraction shortening (FS), the parameters of cardiac contractile function, were reduced in miRNA-128$^{OE}$ hearts (FIG. 2H). In contrast, Dox treatment did not induce cardiac dysfunction in Ctrl mice (data now shown).

Figure 2I:
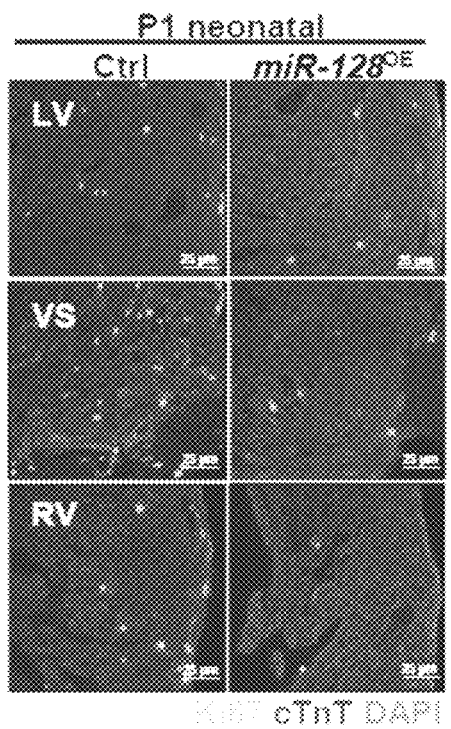
Figure 2J:
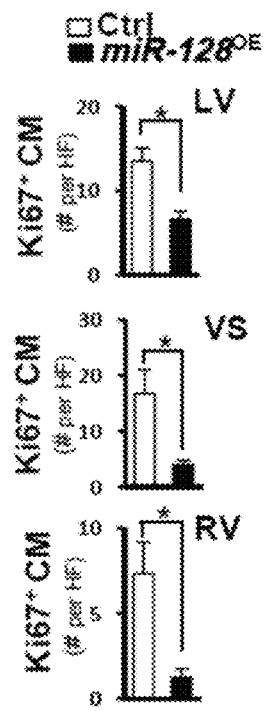

To explore the cellular mechanisms underlying the observed hypertrophy, heart sections were immunostained to assess proliferation and apoptosis. The miRNA-128$^{OE}$ hearts displayed diminished proliferation of CMs based on the reduced number of Ki67$^+$ CMs compared with Ctrl (FIG. 2I and FIG. 2J). However, there was no significant increase in apoptotic CMs in miRNA-128$^{OE}$ hearts when assessed by TUNEL staining (FIG. 2C). Interestingly, miRNA-128$^{OE}$ mice displayed pathologically dilated cardiomyopathy that was consistent with focal replacement fibrosis, CM hypertrophy, and severe heart failure compared with Ctrl mice at the same adult stage (data not published). Taken together, these data indicate that CM-specific overexpression of miRNA-128 induces early CM cell cycle exit and compensatory pathological growth of CM (hypertrophy), and impaired cardiac homeostasis.

Example 3

This Example Illustrates that Deletion of miRNA-128 Stimulates Postnatal CM Proliferation.

Figure 3A:
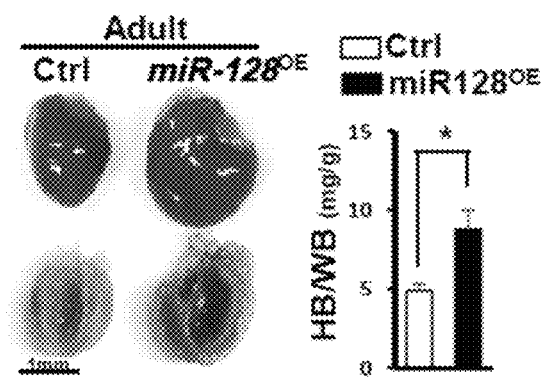
FIG. 3A) overexpression of miRNA-128 induce dilated cardiomyopathy, gross morphology of adult (4 months old) hearts (left), Heart weight (HB) to body weight (BW) ratio (right), (n=5)
Figure 3B:
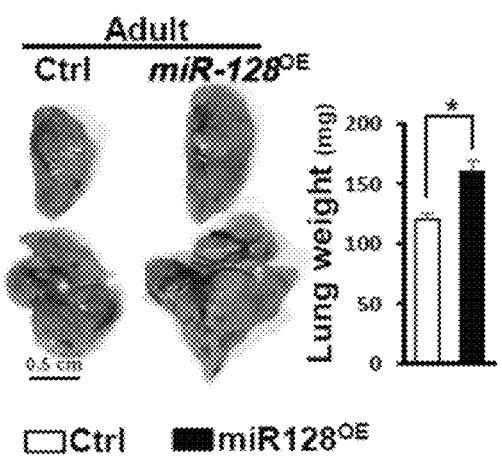
FIG. 3B) gross morphology of lung (left), quantification data of lung weight (n=5)
Figure 3C:
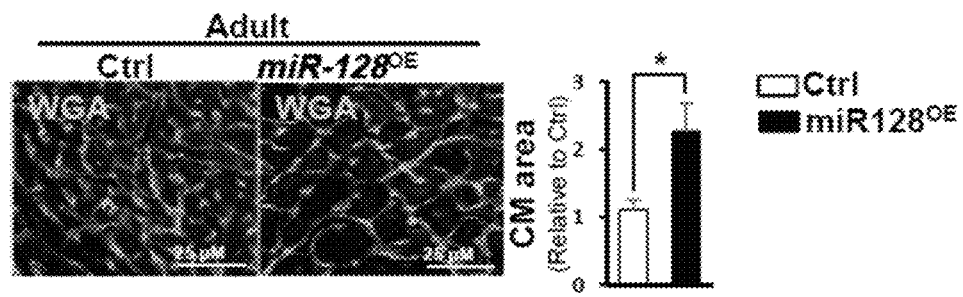
FIG. 3C) wheat germ agglutinin (WGA) staining of hearts (left), quantification of CM size as measured by WGA staining (right) (n=6)
Figure 3D:
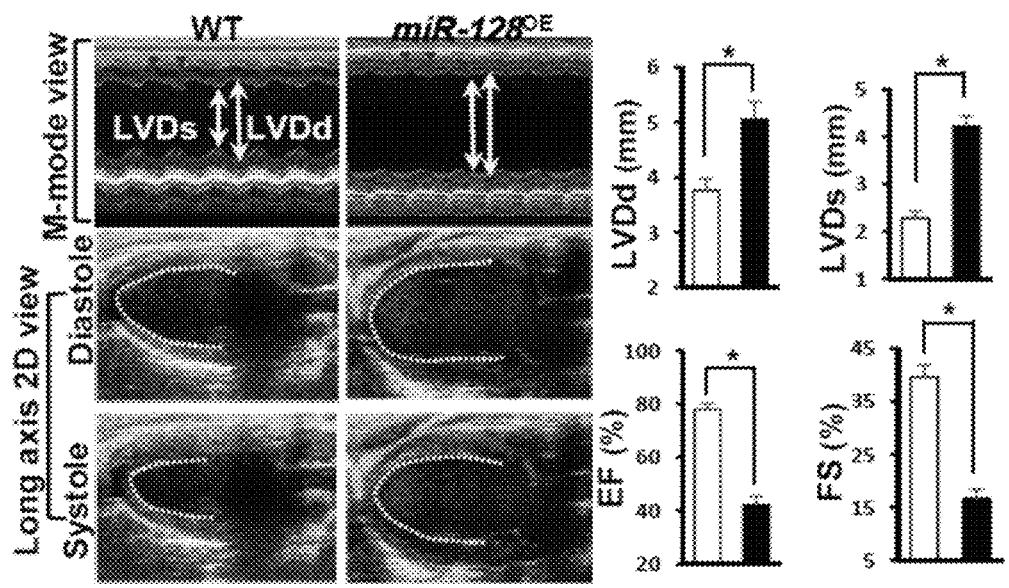
FIG. 3D) heart function analyzed by echocardiography in adult mice, as measured by left ventricular diastolic diameter (LVDd), systolic diameter (LVDs), ejection fraction (EF %), and fraction shortening (FS %) (n=6). Statistical significance was calculated using Student's t-test. Data are means±SEM. *P<0.05.

Having established a correlation between miRNA-128 overexpression and inhibition of CM proliferation, the question of whether loss of miRNA-128 is causal for CM proliferation arises. When miRNA-128 was knocked down in cultured neonatal rat CMs in vitro using specific miRNA-128 inhibitor (designated as Anti-miRNA-128) (FIG. 3A), the CMs became dedifferentiated, based on sarcomere disassembly assessed by immunostaining for Cardiac troponin T (cTnT), the sarcomere structure marker (FIG. 3B-FIG. 3D). Consistent with sarcomere disassembly, qPCR showed that expression of sarcomere genes (Myh6 and cTnT) was reduced (data not shown). In addition to inducing dedifferentiation, silencing of miRNA-128 increased the number of mitotic CMs as determined by immunostaining for phosphorylated histone3 (pH3$^+$) as compared with control CMs (Ctrl) (FIG. 3E and FIG. 3G). Silencing of miRNA-128, however, did not induce apoptosis in these cells (FIG. 3F and FIG. 3G).

Figure 4A:
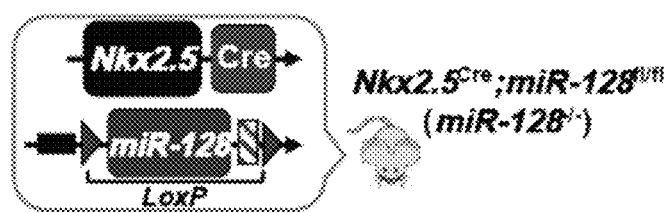
FIG. 4A) Cardiac miRNA-128 deletion promoted postnatal CM proliferation without cardiac dysfunction, a schematic diagram depicting the generation of cardiac-restricted miRNA-128 knockout (miRNA-128$^{-/-}$) mice.
Figure 4B:
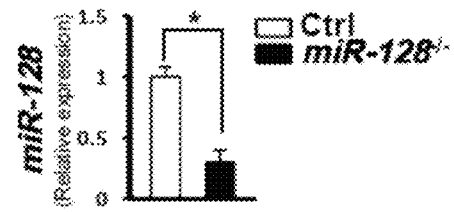
FIG. 4B) qPCR analysis of miRNA-128 expression in Ctrl (miRNA-128$^{fl/fl}$) and miRNA-128$^{-/-}$ hearts (n=6)

Given the evidence that silencing of miRNA-128 induces CM proliferation in vitro, the next step is to determine what effects the deletion of miRNA-128 would have on CM proliferation in vivo. Cardiac-specific conditional miRNA-128 knockout mouse were generated by crossing miRNA-128$^{flox/flox}$ (miRNA-128$^{fl/fl}$) mice (FIG. 4A) with Nkx2.3$^{Cre}$ mice, resulting in deletion of miRNA-128 during cardiogenesis (Nkx2.5$^{Cre}$: miRNA-128$^{fl/fl}$ mice, designated as miRNA-128$^{-/-}$) (FIG. 4B). Hearts from miRNA-128$^{fl/fl}$ (Control mice, Ctrl) and miRNA-128$^{-/-}$ mice were harvested and analyzed at P7, at the time when most CMs have exited the cell cycle and become post mitotic. Downregulation of miRNA-128 in hearts from miRNA-128$^{-/-}$ mice was confirmed by qPCR (FIG. 3A-FIG. 3B). Phenotypic characterization of miRNA-128$^{-/-}$ mice at P7 demonstrated that heart size (FIG. 3C) and heart function by echocardiography (FIG. 3E) were unaffected by miRNA-128 deletion. Although the heart weight-to-body weight ratio (HB/WB) of miRNA-128$^{-/-}$ and Ctrl mice at P7 was similar (FIG. 3D), CMs in miRNA-128$^{-/-}$ hearts were smaller (FIG. 3F). This could indicate an increased number of CMs in these hearts due to persistent proliferation resulting from miRNA-128 deletion. To test this proposition, CMs were stained with Ki67 to assess the number of cycling cells. The results show that loss of miRNA-128 results in a striking increase in CM proliferation (FIG. 3G-FIG. 3H). Sarcomere disassembly, a characteristic of CM dedifferentiation and proliferation, was also prominent in miRNA-128$^{-/-}$ hearts compared with Ctrl group (FIG. 3G and FIG. 3I). In addition to the CMs with disassembled sarcomeres, a significantly higher number of Ki67-positive cells were identified in miRNA-128$^{-/-}$ hearts (FIG. 3J). No obvious CM apoptosis was observed in miRNA-128$^{-/-}$ hearts (data not shown). By 5-ethynyl-2'-deoxyuridine (EdU) incorporation assay (FIG. 3K-FIG. 3N), we also found a significant increase in the number of EdU$^+$ CMs in miRNA-128$^{-/-}$ hearts at P14 (FIG. 3K-FIG. 3L) as well as P21 (FIG. 3M-FIG. 3N) when compared with Ctrl. These mice developed normally to adulthood without compromised cardiac dysfunctions (FIG. 5 A-B). These data suggested that miRNA-128 deletion is sufficient to extend the postnatal CM proliferation window.

Example 4

This Example Demonstrates that Cardiac miRNA-128 Deletion Reconfigures Cell Cycle-Related Gene Expression in the Postnatal Heart.

Figure 4C:
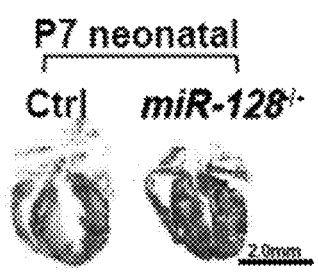
FIG. 4C) Masson Trichrome staining of mouse hearts at P7.
Figure 4D:
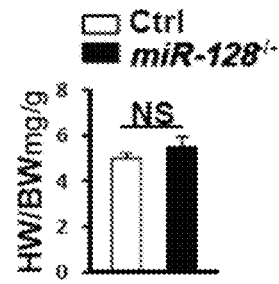
FIG. 4D) heart weight (HW) to body weight (BS) ratio in Ctrl and miRNA-128$^{-/-}$ mice (n=6)
Figure 4E:
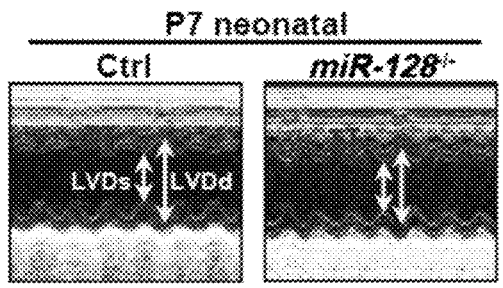
FIG. 4E) cardiac function analyzed by left ventricular ejection fraction (EF %) and fraction shortening (FS %) (n=6)
Figure 4F:
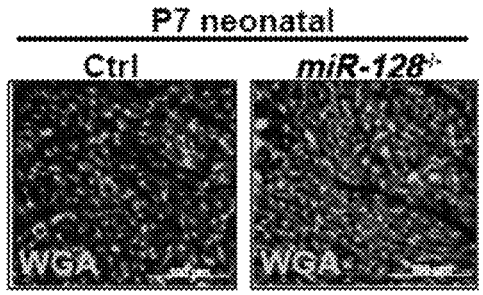
FIG. 4F) cell size determined by wheat germ agglutinin (WGA) staining (n=6)

To identify miRNA-128 target genes that may be responsible for CM proliferation, online databases TargetScan and miRanda and others were mined with selective focus on genes that were downregulated in adult hearts relative to neonatal hearts. The data predicted that Suz12, the core component of polycomb repressive complex 2 (PRC2), is a putative miRNA-128 target (FIG. 4A). When assayed by Western blotting, the levels of SUZ12 were lower in the adult heart than in the neonatal heart (FIG. 4B-C), consistent with this prediction. To investigate whether miRNA-128 regulates Suz12 expression, mouse neonatal CM were transfected with a negative control (Ctrl), a mimic of miRNA-128 (miRNA-128), or an inhibitor of miRNA-128 (Anti-miRNA-128) and assessed for the level of SUZ12 by Western blotting. Overexpression of miRNA-128 significantly reduced the protein level of SUZ12, whereas inhibition of miRNA-128 led to its increased expression (FIG. 4D-E). To further test whether miRNA-128 regulates Suz12 expression, a vector containing a luciferase reporter vector with a DNA sequence encoding the complete 3' untranslated region (3'UTR) from mouse Suz12 (designated as WT), and a mutated vector (designated as Mut) containing mismatches in the predicted miRNA-128 binding site in the 3'UTR (FIG. 4F) were constructed. Co-transfection of HEK293T cells with the Suz12 3'UTR plasmid (WT) and miRNA-128 mimic resulted in a significant decrease in luciferase activity compared with cells co-transfected with negative control or the mutated 3'UTR target sequence (Mut), indicating that Suz12 is a direct target of miRNA-128.

Figure 4G:
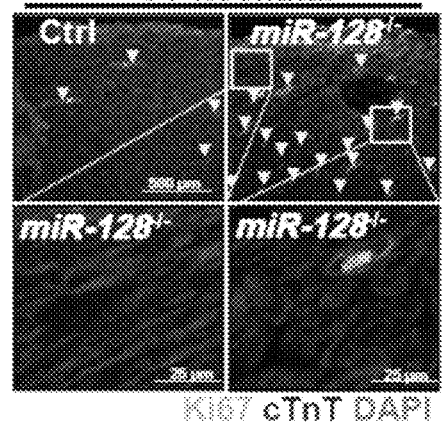
FIG. 4G) Evaluation of CM cell-cycle activity and sarcomere structure in P7 hearts by immunofluorescence analysis of cTnT and Ki67.
Figure 4H:
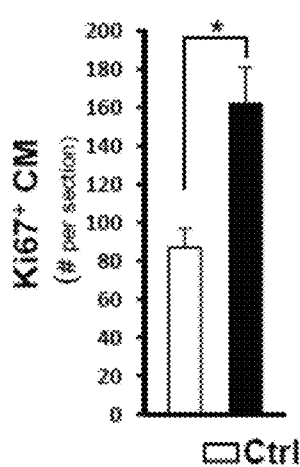
FIG. 4H, FIG. 4I, and FIG. 4J) quantification of Ki67+CM, sarcomere disassembled CM and Ki67$^+$ disassembled CM (n=6)
Figure 4I:
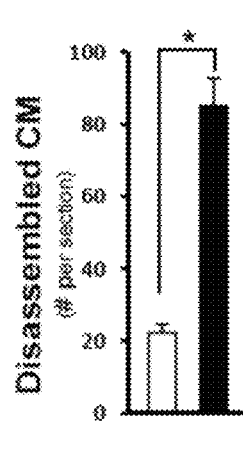

To better delineate how the miRNA-128-Suz12 interaction might mediate cell proliferation in vivo, the expression of cell-cycle related genes in miRNA-128$^{-/-}$ hearts at P7 was analyzed. As predicted, the level of SUZ12 was elevated in miRNA-128$^{-/-}$ P7 hearts compared with control mice (Ctrl) while CDKi p27 target was downregulated (FIG. 4G-H). SUZ12 can catalyze the trimethylation of histone H3K27 to H3K27me3, a transcriptional repressive mark. Since SUZ12 appears to be regulated by miRNA-128, it was hypothesized that in miRNA-128-deficient hearts SUZ12 should be associated with H3K27me3 and directly repress the transcription of genes encoding cell cycle inhibitors. When assayed by chromatin immunoprecipitation (ChIP)-qPCR, SUZ12 and H3K27me3 were significantly enriched on the p27 promoter in miRNA-128$^{-/-}$ hearts compared with hearts from Ctrl mice (FIG. 4I).

Figure 4J:
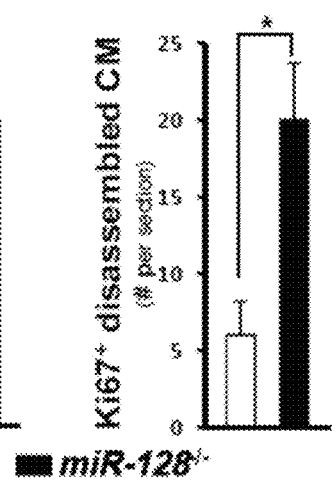
Figure 4K:
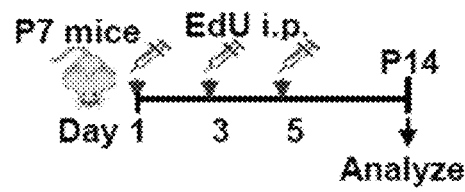
FIG. 4K) a schematic diagram depicting EdU intraperitoneal (i.p) injection to label the proliferating CM.
Figure 4L:
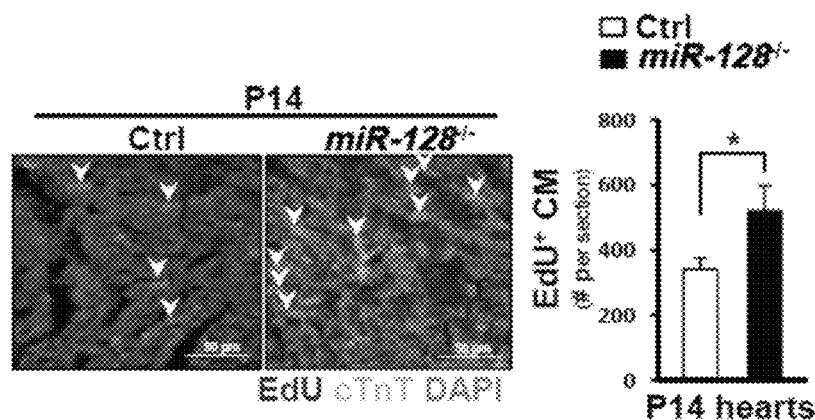
FIG. 4L) representative image of EdU+ CM in Ctrl hearts and MiRNA-128$^{-/-}$ hearts at P14.
Figure 4M:
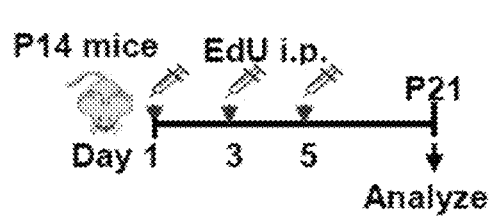
FIG. 4M) schematic diagram depicting EdU i.p injection to label the proliferating CM.
Figure 4N:
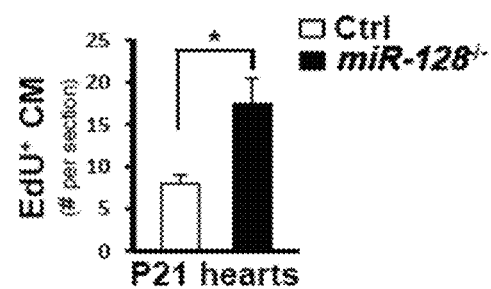
FIG. 4N) quantification of EdU+ CM on P21 hearts.
Figure 4O:
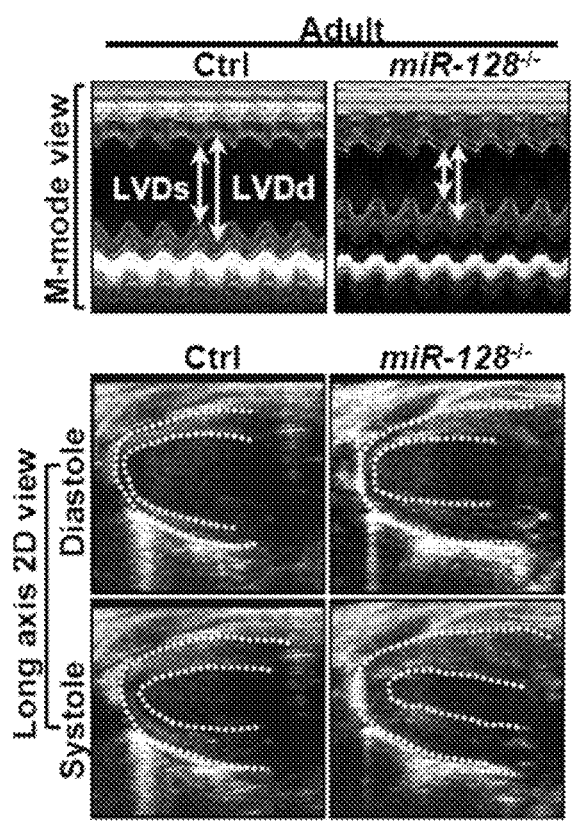
FIG. 4O and FIG. 4P) cardiac miRNA-128 deletion promoted postnatal CM proliferation without cardiac dysfunction, heart function analyzed by echocardiography in adult mice, as measured by left ventricular diastolic diameter (LVDd), systolic diameter (LVDs), ejection fraction (EF %), and fraction shortening (FS %) (n=6). Statistical significance was calculated using Student's t-test. Data are means±SEM. *P<0.05.
Figure 4P:
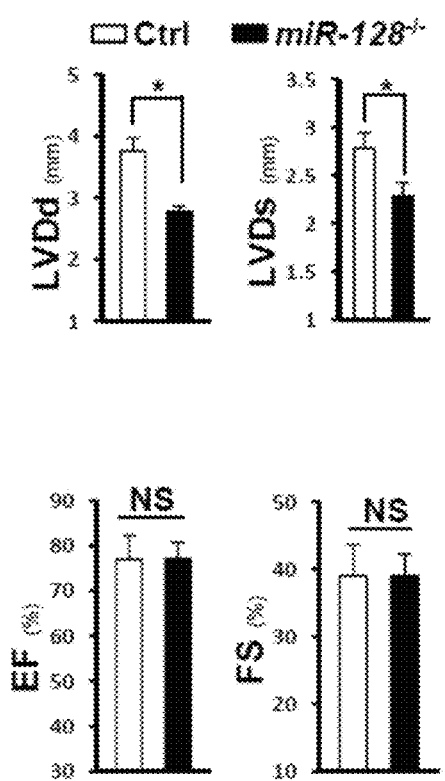

Since miRNA-128 seems to exerts its inhibitory effects by recruiting SUZ12 to the promoters of the gene encoding cell cycle effectors and repressing their expression, the question of whether targeting of Suz12 by miRNA-128 is sufficient to account for the enhanced proliferation observed in miRNA-128$^{-/-}$ CMs was examined. Direct inhibition of Suz12 by siRNA (si-Suz12) in miRNA-128$^{-/-}$ neonatal mouse hearts reversed the pro-proliferative effect imparted by miRNA-128 deletion (miRNA-128$^{-/-}$), as evidenced by a significant decrease in the number of Ki67$^+$ CMs in si-Suz12 group in contrast to control group (si-Ctrl)(FIG. 4J-K). Collectively, these data indicated that miRNA-128 deletion stimulates proliferation of CMs, in part through epigenetic modulation of cell-cycle related genes via targeting of Suz12 (FIG. 4L).

Example 5

This Example Illustrates that Overexpression of miRNA-128 Inhibits Neonatal Cardiac Regeneration after Injury.

Figure 6A:
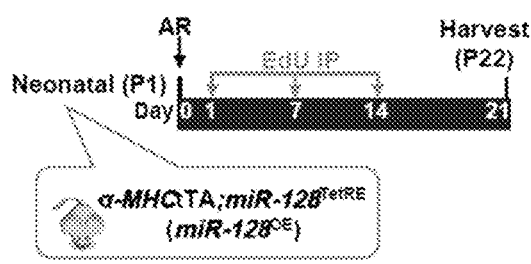
FIG. 6A) miRNA-128 overexpression inhibits neonatal cardiac regeneration after injury; sets forth a schematic diagram depicting the generation of apex resection (AR) model in miRNA-128 overexpressing mice (miRNA-128$^{OE}$)
Figure 6B:
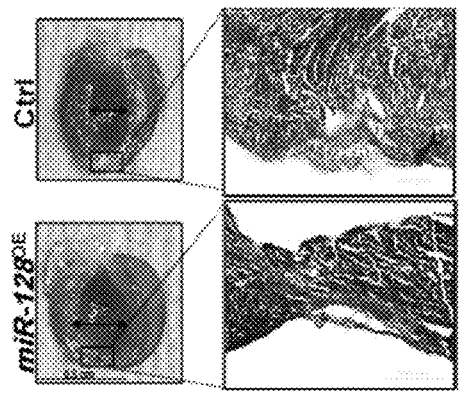
FIG. 6B) Masson trichrome staining for Ctrl (miRNA-128$^{TetRE}$) and miR128$^{OE}$ hearts at day 21 after AR.
Figure 6C:
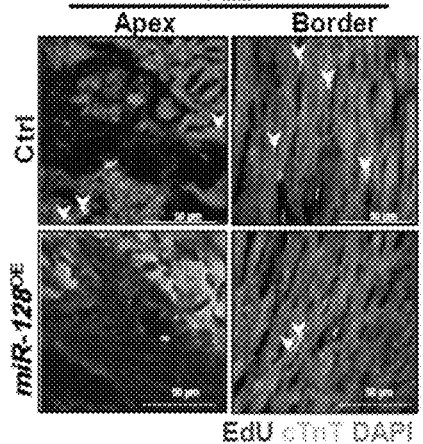
FIG. 6C) evaluation CM proliferation by EdU incorporation assay.
Figure 6D:
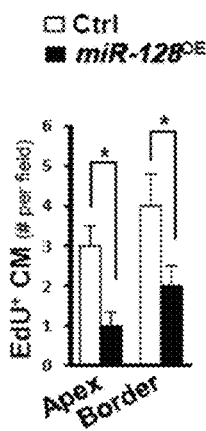
FIG. 6D) Quantification of EDU+ CM in Pa hearts at day 21 post AR (n=6)

To enable assessment of temporal gene expression during cardiac regeneration an apex resection (AR) model in neonatal mice at P1 was developed (FIG. 6A). Histological analysis verified that by day 7 post-AR, the initial large blood clot in the apex had been replaced by newly formed CMs and limited fibrotic tissue (FIG. 6B). Also at day 7 post-AR, genes associated with cell proliferation were significantly activated, whereas miRNA-128 expression was significantly diminished (FIG. 6C-D). These data imply that downregulation of miRNA-128 was associated with neonatal heart regeneration.

Figure 5A:
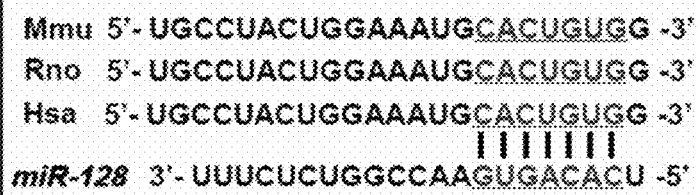
FIG. 5A) miRNA-128 deletion coordinates activation of cell cycle-related genes, shows the predictive conserved target site of miRNA-128 in 3'UTR of SUZ12 within different species.
Figure 5B:
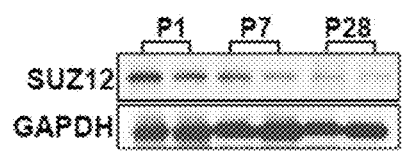
FIG. 5B) western blotting analysis of SUZ12 expression in mouse hearts at P1, P7, and P28.
Figure 5C:
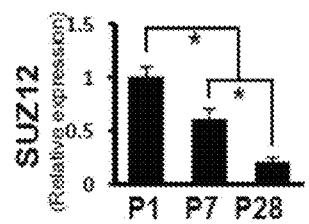
FIG. 5C) Quantification of SUZ12 expression in P1, P7, and P28 hearts (n=5)
Figure 5D:
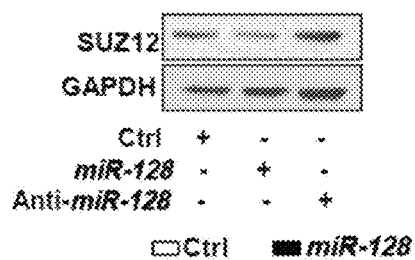
FIG. 5D and FIG. 5E) western blotting analysis of SUZ12 expression in neonatal CMs treated with either vehicle (Ctrl), miRNA-128 mimic (miRNA-128) or miRNA-128 inhibitor (Anti-128) (n=3)
Figure 5E:
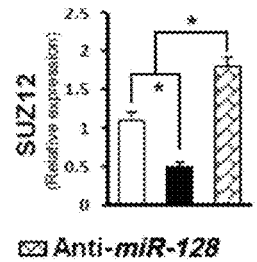
Figure 5F:
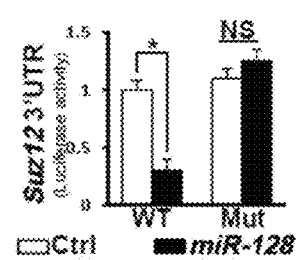
FIG. 5F) Luciferase reporter assay for wild type and mutant Suz12 3' UTR in cells treated with either vehicle (Ctrl) or miRNA-128 inhibitor (Anti-128) (n=3)
Figure 5G:
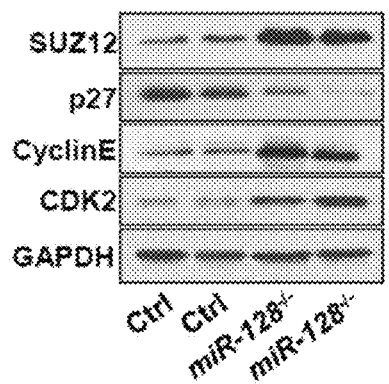
FIG. 5G-FIG. 5H) western blot assay for cell cycle-related protein expression in Ctrl and miRNA-128$^{-/-}$ hearts at P7 (n=5)
Figure 5H:
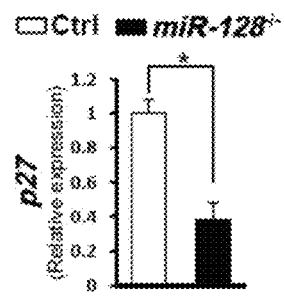
Figure 5I:
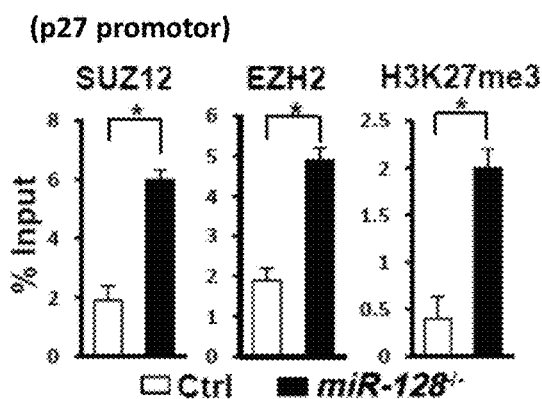
FIG. 5I) ChIP-qPCR assay for SUZ12, EZH2, and H3K27me3 enrichment on the p27 promoter (n=5)
Figure 5J:
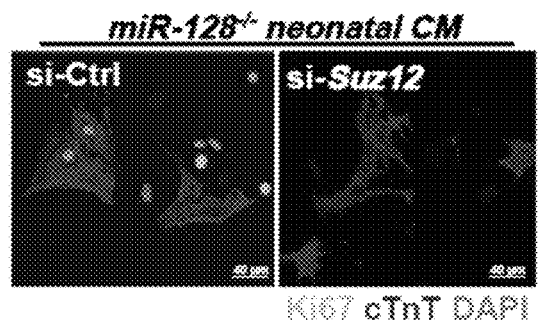
FIG. 5J) evaluation of cell proliferation by immunofluorescence staining of Ki67 in miRNA-128$^{-/-}$ neonatal CM transfected with either control siRNA (si-Ctrl) or SUZ12 siRNA (si-Suz12)
Figure 5K:
FIG. 5K) Quantification of CM proliferation by Ki67 immunostaining (n=5)
Figure 5L:
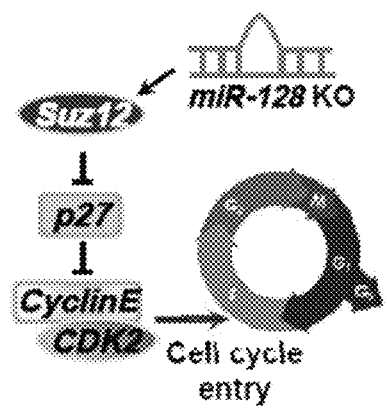
FIG. 5L) Proposed model of miRNA-128 deletion promoting CM proliferation through coordinating the expression cell cycle-related genes. Statistical significance was calculated using ANOVA in C, E, and K and Student's t-test in F, H, and I. Data are means±SEM. *P<0.05.

To test whether miRNA-128 regulates cardiac regenerative capacity in neonatal mice, the miRNA-128$^{OE}$ mouse model in which miRNA-128 is overexpressed in a CM specific and temporally controlled (by Dox withdrawal) manner was utilized (FIG. 5A). The miRNA-128$^{OE}$ mice and control miRNA-128$^{TetRE}$ mice (Ctrl) were subjected to AR at P1, and hearts from both groups were examined histologically. At 21 days post-AR, the miRNA-128$^{OE}$ hearts showed left ventricle dilation and defective regeneration compared with Ctrl groups (FIG. 5B). The miRNA-128$^{OE}$ hearts showed fewer proliferating CMs, as quantified by the decreased number of EdU$^+$ CM nuclei in the injured apex and border area (FIG. 5C and FIG. 5D), and a greater extent of CM hypertrophy (FIG. 5E). In addition, systolic function was significantly impaired in the miRNA-128$^{OE}$ group relative to Ctrl group (FIG. 5F and FIG. 5G). These findings suggest that inhibition of CM proliferation by miRNA-128 overexpression is sufficient to impair cardiac regeneration in a neonatal mouse model.

Example 6

Figure 6E:
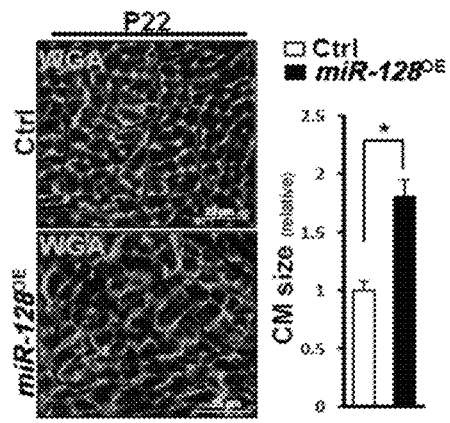
FIG. 6E) wheat germ agglutinin (WGA) staining in mouse hearts at day 21 after AR.
Figure 6F:
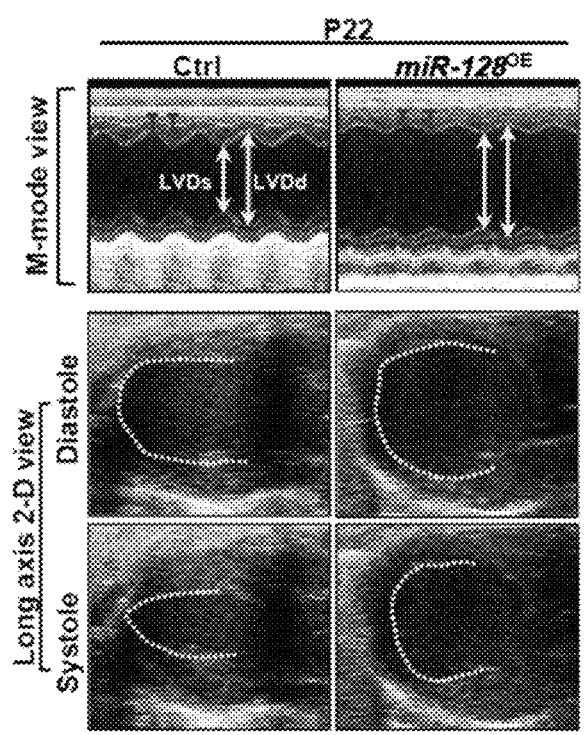
FIG. 6F-FIG. 6G) heart function analyzed by echocardiography and quantification by left ventricular diastolic diameter (LVDd), systolic diameter (LVDs), ejection fraction (EF %), and fraction shortening (FS %) (n=6). Statistical significance was calculated using Student's t-test in D, F, and G. Data are means±SEM. *P<0.05.
Figure 6G:
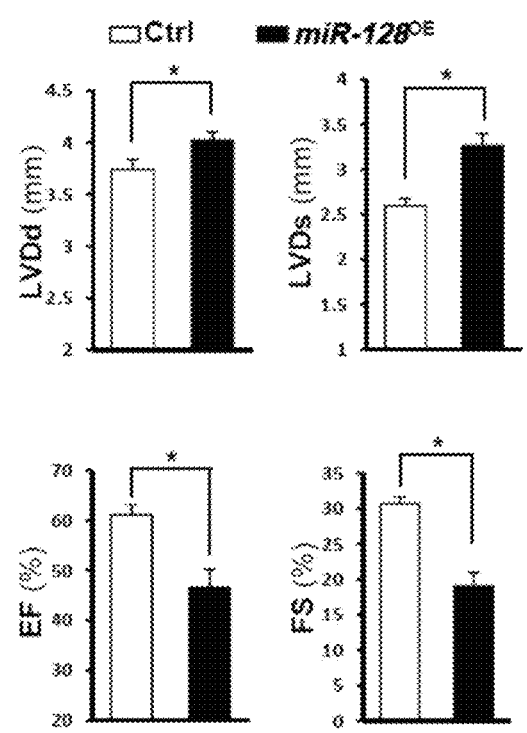

This Example Demonstrates that Deletion of miRNA-128 Increases CM Proliferation and Promotes Adult Cardiac Regeneration To investigate whether loss of miRNA-128 in the adult is capable of promoting CM proliferation, a cardiac specific, tamoxifen (TAM) inducible miRNA-128 knockout mice was then generated by crossing α-MHC$^{MerCreMer}$ mice with miRNA-128$^{fl/fl}$ mice (FIG. 6A). TAM was administered at P21 to induce miRNA-128 knockout at adult stage. The adult miRNA-128-deleted mice were designated iKO, and the knockout was validated by qPCR. Phenotypic characterization showed that neither heart size nor function was affected in the iKO mice by miRNA-128 deletion (data not shown). The heart weight-to-body ratio (HB/WB) was unchanged in iKO mice. Staining with WAG, however, showed that the size of the iKO CMs was smaller than the control CMs (FIG. 6C-E), suggesting that loss of miRNA-128 in the adult heart increase the number of CMs. This increase in CM number following miRNA-128 deletion was further confirmed by analysis of EdU incorporation into CMs (FIG. 6B). Furthermore, the total number of adult CMs and percentage of mono-nucleated CMs was significantly increased in iKO hearts 2 weeks after TAM induced miRNA-128 deletion (FIG. 6F-G).

Figure 7A:
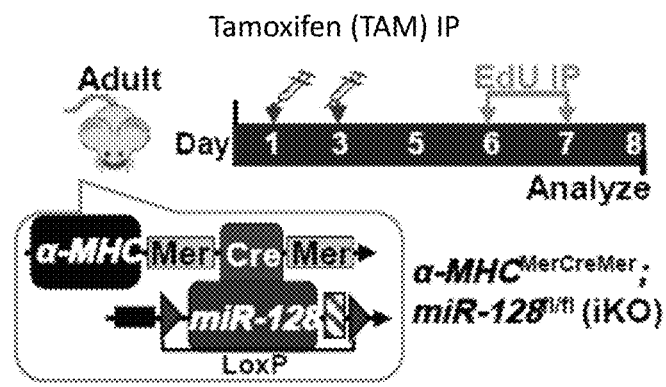
FIG. 7A) miRNA-128 deletion promoted adult CM dedifferentiation and proliferation, sets forth a schematic diagram depicting TAM-inducible miRNA-128 deletion (iKO) in adult hearts (P56)
Figure 7B:
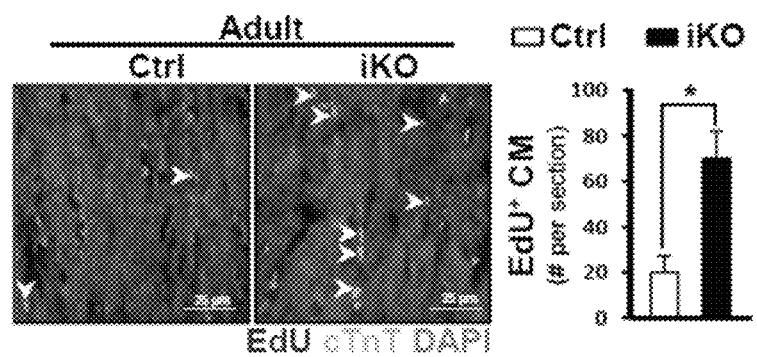
FIG. 7B) evaluation of CM proliferation by EdU incorporation assay (n=6)
Figure 7C:
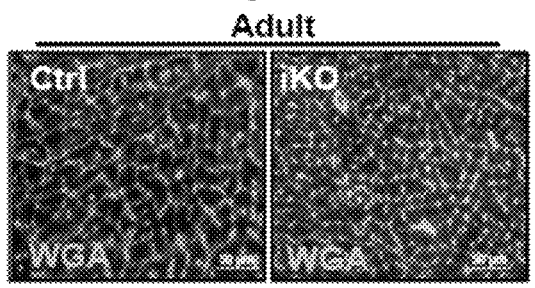
FIG. 7C) wheat germ agglutinin (WGA) staining in Ctrl and iKO hearts (n=6)
Figure 7D:
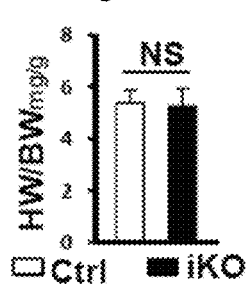
FIG. 7D) quantification data of heart weight to body weight ratio (HW/BW) (n=6)

To determine whether cells in the myocardial lineage dedifferentiate following deletion of miRNA-128, a TAM inducible dual-lineage tracing system was generated by crossing α-MHC$^{MerCreMer}$ mice with miRNA-128$^{fl/fl}$ mice followed by crossing with Rosa26-tdTomato reporter mice to produce α-MHC$^{MerCreMer}$; miRNA-128$^{fl/+}$; R26R-tdTomato mice (designated as iKO-tdTomato) (FIG. 6H). In these transgenic mice, miRNA-128-deficient CMs were labeled red (tdTomato, red fluorescence) following TAM administration. After TAM-induced miRNA-128 deletion (FIG. 6J), the α-MHC myocardial lineage positive CMs in iKO-tdTomato mouse displayed a disorganized sarcomere structure and reduced sarcomere-related gene expression compared with control mice (α-MHC$^{MerCreMer}$; R26R-tdTomato, designated as Ctrl-tdTomato) (FIG. 6J and FIG. 6K). No apoptosis was observed in hearts from iKO-tdTomato mice (FIG. 7A-B). There was, however, increased expression of genes associated with cell proliferation (Nuspa1, RacGap1 andMyh10) and fetal genes associated with negative regulation of CM differentiation (Nppa and Ngpb) in iKO-tdTomato hearts detected by qPCR (FIG. 6K). However, in iKO mice, cardiac morphology remained unchanged and heart functions were normal (FIG. 7C-D). These results indicate that deletion of miRNA-128 in the adult heart results in dedifferentiation of CMs and reentry of CMs into the cell cycle.

Figure 7E:
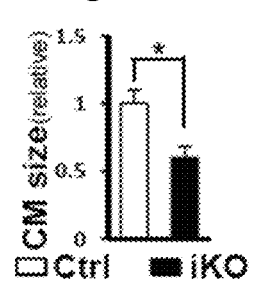
FIG. 7E) quantification data of cell size determined by WGA staining (n=6)
Figure 7F:
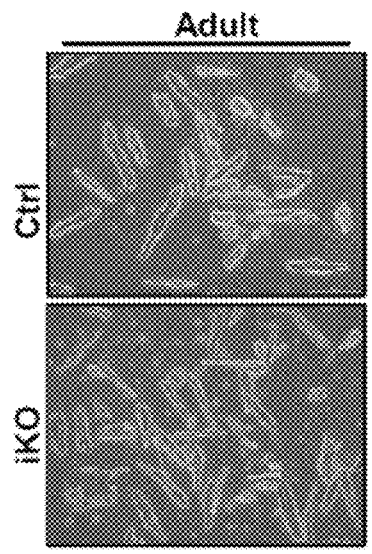
FIG. 7F) representative images of isolated adult CMs in Ctrl and iKO hearts.
Figure 7G:
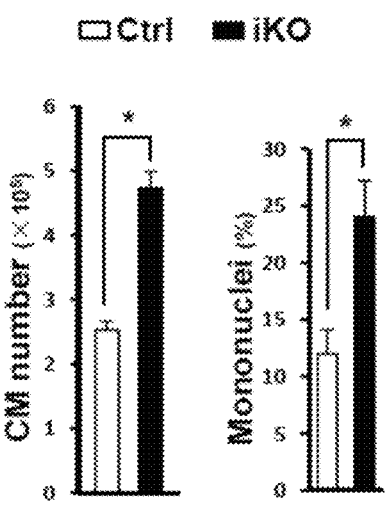
FIG. 7G) quantification of CM number in Ctrl and iKO mouse (n=6)
Figure 7H:
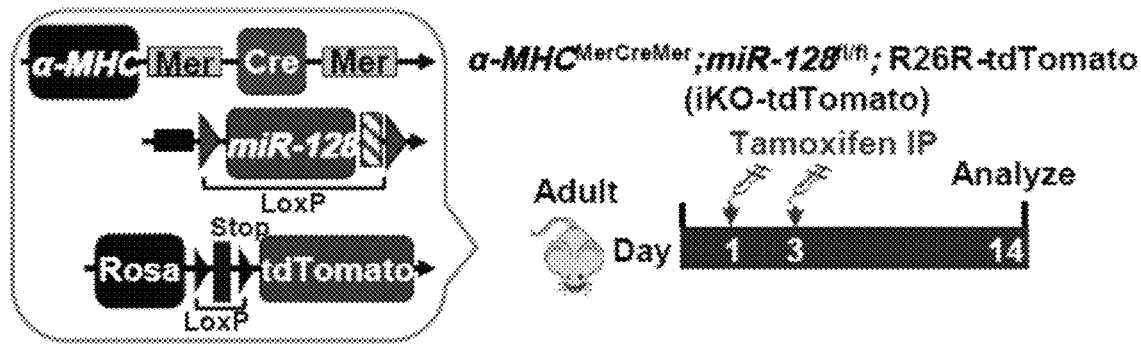
FIG. 7H) schematic of TAM-inducible dual-lineage tracing transgenic mouse model (α-MHC$^{MerCreMer}$:MiRNA-128$^{fl/fl}$:Rosa-tdToamto, designated as iKO-tdTomato)
Figure 7I:
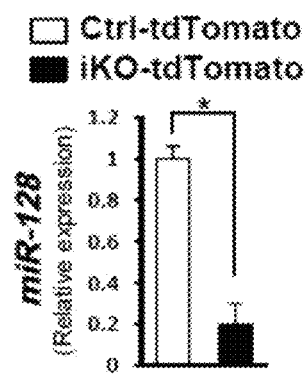
FIG. 7I) qPCR data of miRNA-128 expression in hearts (n=5)
Figure 7J:
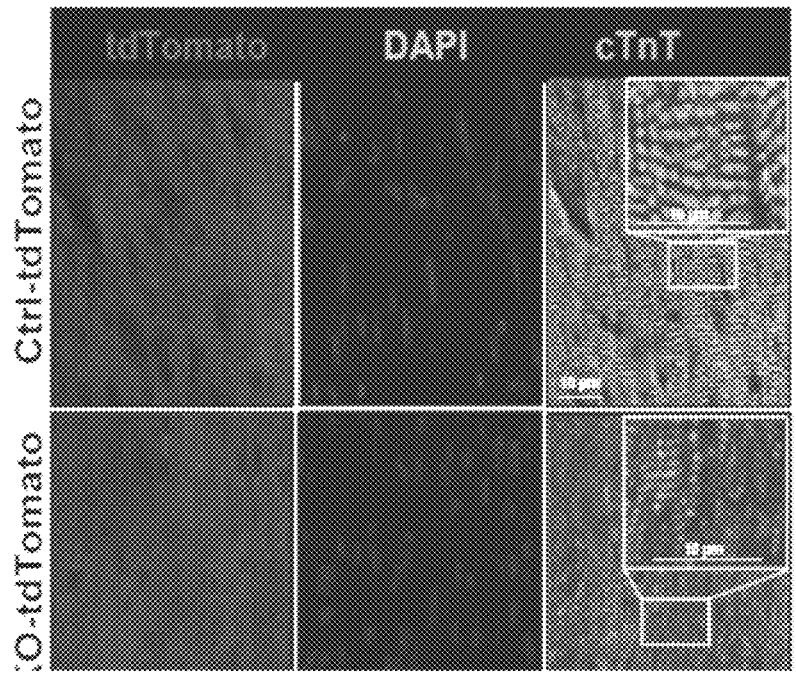
FIG. 7J) in vivo sarcomere structure analysis by CtnT immunofluorescence staining (n=6)
Figure 7K:
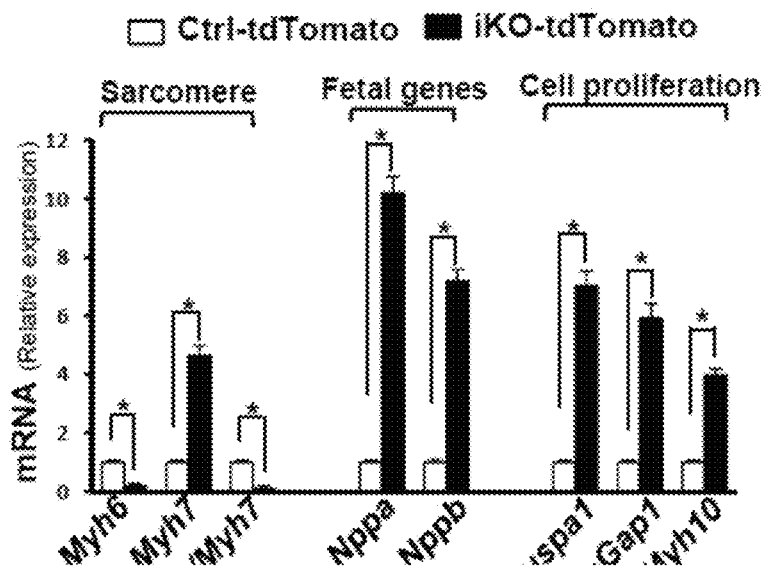
FIG. 7K) qPCR analysis of gene expression in adult hearts, including sarcomere gene, fetal gene, and cell proliferation associated gene (n=6). Statistical significance was calculated using Student's t-test in B, D, E, G, I, and K. Data area means±SEM. *P<0.05. NS=not significant.
Figure 8A:
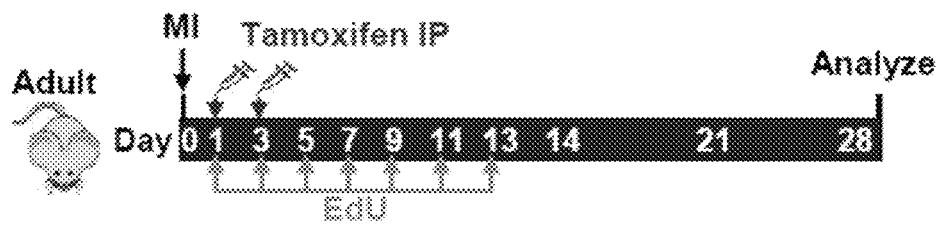
FIG. 8A) miRNA-128 deletion promoted adult cardiac regeneration after MI, the experimental design for adult cardiac regeneration analysis following MI in TAM-inducible miRNA-128 knockout (iKO) mice.
Figure 8B:
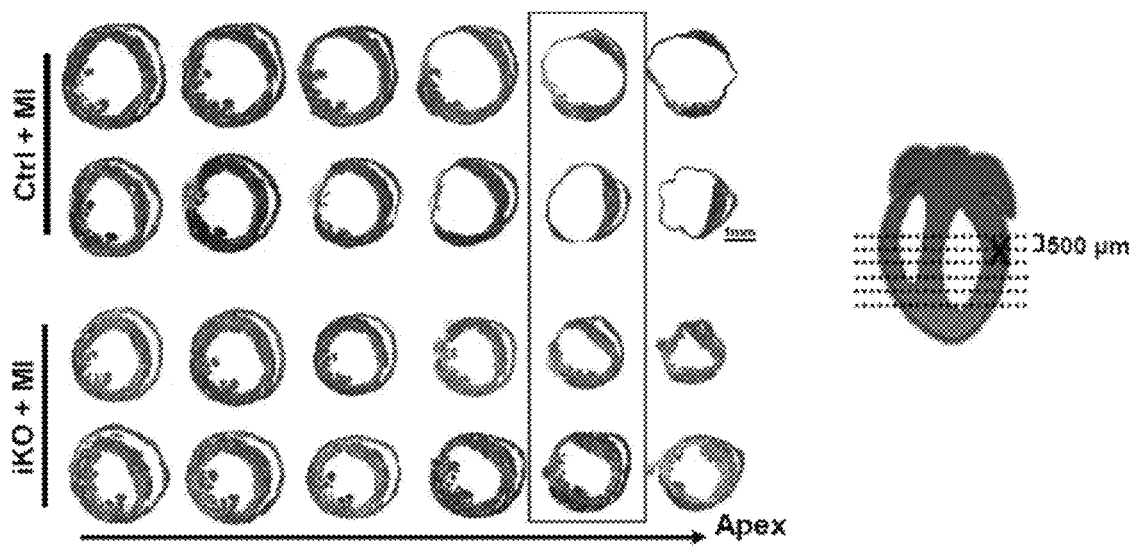
FIG. 8B) Masson's Trichrome-stained hearts at 28 days after MI, serial sections were cut at 500 μm intervals.
Figure 8C:
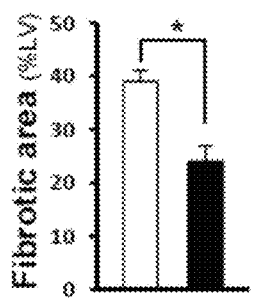
FIG. 8C) quantification of the fibrotic areas in heart section (n=8)
Figure 8D:
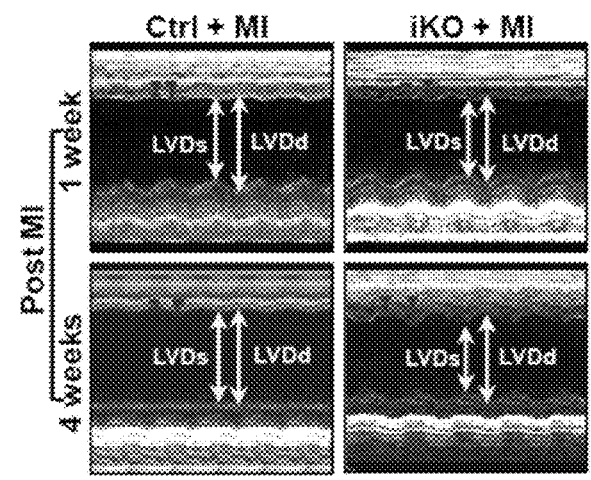
FIG. 8D and FIG. 8E) heart function analyzed by echocardiography and quantified by left ventricular diastolic diameter (LVDd), LV systolic diameter (LVDs), ejection fraction (EF %), and fraction shortening (FS %). Statistical significance was calculating using Student's t-test in C and E. Data area means±SEM. *P<0.05. NS=not significant.
Figure 8D:
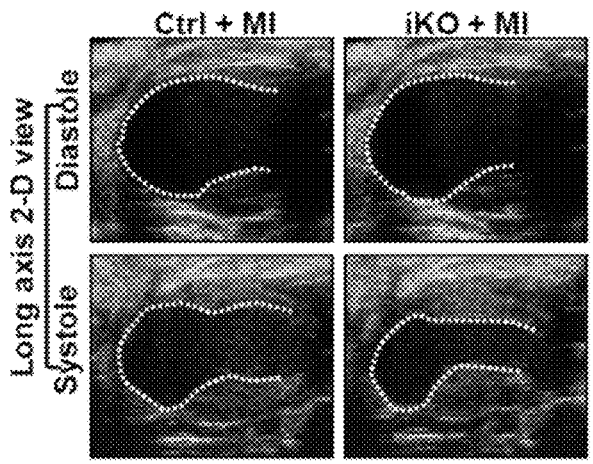
Figure 8E:
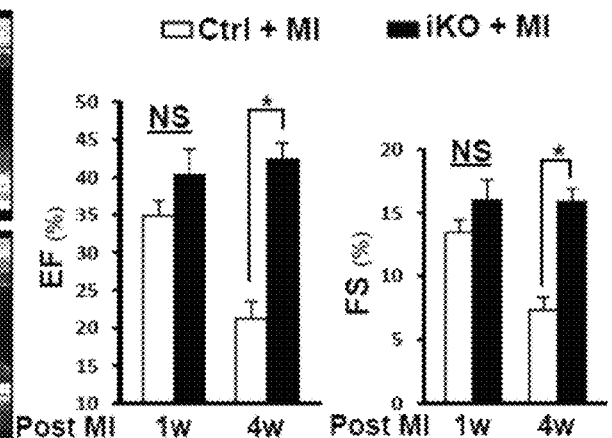
Figure 8E:
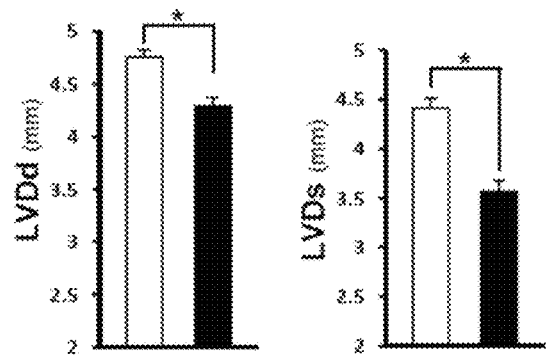
Figure 9:
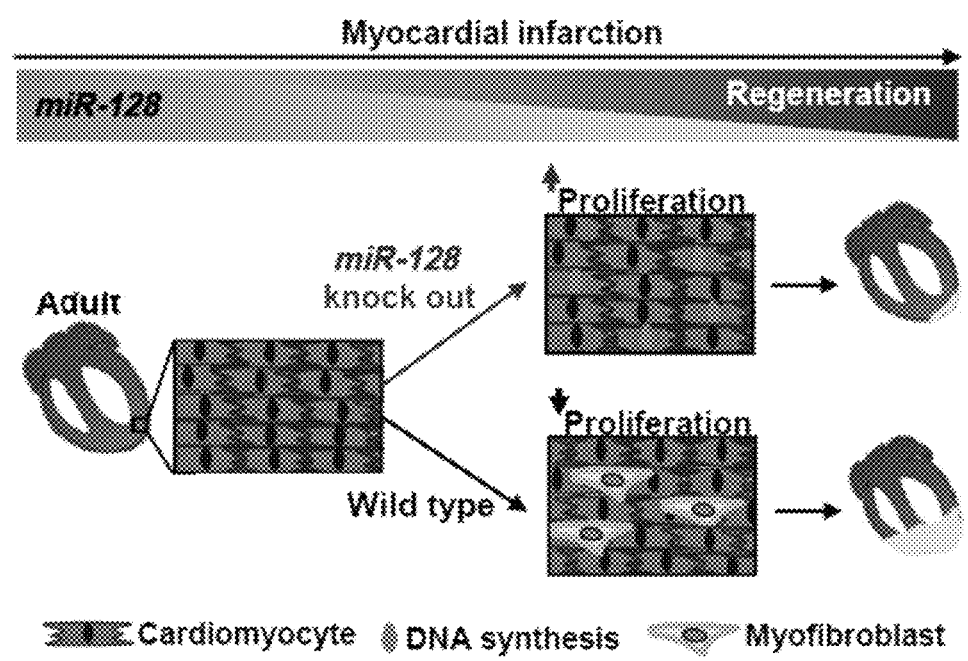
FIG. 9) sets forth a schematic diagram showing that miRNA-128 inhibition activates endogenous cardiac regeneration by promoting cardiomyocyte proliferation in an infarcted heart.

To determine whether induction of cardiac proliferation following miRNA-128 deletion in adult mice is sufficient to allow adult heart repair following MI, we subjected adult iKO mice to permanent ligation of the left anterior descending coronary artery (LAD). One day after MI, TAM was administered to delete miRNA-128 in CMs (FIG. 7A). Seven days after the MI, a decrease in CM death (FIG. 8B) and increased proliferation in iKO hearts was detected (FIG. 8C-D). In the iKO hearts, analysis of sarcomere structures revealed robust dedifferentiated cardiac muscle in border areas and remote areas, and analysis of EdU incorporation was indicative of increased DNA synthesis (FIG. 8C). In addition to dedifferentiation and enhanced proliferation (FIG. 8D) iKO hearts showed significantly less fibrosis than Ctrl groups 4 weeks after MI (FIG. 7B-C). Similarly, diminished cardiac function was significantly reversed in iKO mice, as evidenced by increased ejection fraction (EF) and fractional shortening (FS) after MI when compared with the Ctrl animals (FIG. 7D-E). Cardiac remodeling was also significantly reversed in iKO mice with reduced LVDd and LVDs (FIG. 7D). Collectively, these data indicate that inhibition of miRNA-128 promotes CM proliferation and improved endogenous cardiac regeneration after MI (FIG. 7F).

The following protocols apply to one or more of the examples disclosed herein.

Laboratory Animals

All research protocols conformed to the Guidelines for the Care and Use of Laboratory Animals published by the National Institutes of Health (National Academies Press, eighth edition, 2011). All animal use protocols and methods of euthanasia (pentobarbital overdose followed by thoracotomy) used in this study were preapproved by the University of Cincinnati Animal Care and Use Committee. An independent review and approval of cell and chemical drug used in this study was conducted by the Institutional Biosafety Committee (IBC).

Generation of Mice with Conditional Overexpression of miRNA-128

A construct was engineered for knock-in of the miRNA-128 (miRNA-128-3p) gene into Rosa26 locus. A ~1.1 kb and a ~4.3 kb Rosa26 genomic DNA fragments (served as 5' and 3' homology arms, respectively) were amplified from C57BL/6 BAC DNA and cloned into the pBasicLNeoL vector sequentially by in-fusion cloning and confirmed by sequencing. The miRNA-128 gene, under the control of tetO-minimum promoter, was also cloned into the vector in between the two homology arms. In addition, the targeting construct also contains a loxP sites flanked Neomycin cassette for positive selection and a DTA cassette for negative selection. The construct was linearized with ClaI and electroporated into C57BL/6N ES cells. After G418 selection, 7 positive clones were identified from 121 G418 resistant clones by PCR screening. Six positive clones were expanded and further analyzed by Southern blot analysis, among which four clones were confirmed with correct targeting with single copy integration. Correctly targeted ES cell clones were injected into blastocysts, and the blastocysts were implanted into pseudopregnant mice to generate chimeras by Cyagen Biosciences Inc. Chimeric males were bred with Cre delete mice from Jackson Laboratories to generate Neomycin-free knockin mice. The correct insertion of miRNA-128 cassette and the successful removal of Neomycin cassette were confirmed by the PCR assay with the following primers: 5'-TGAGCCAGACCTCCATCGC-3' (SEQ ID NO: 4) and 5'-AGCTCGGTACCATAATCG-3' (SEQ ID NO: 5) for the 559 bp fragment from targeted allele. A PCR with the following primers 5'-ACTC-CAAGGCCACTrATCACC-3' (SEQ ID NO: 6) and 5'-ATGTACCAACTGGGACGACA-3' (SEQ ID NO: 7) was used as an internal control, which amplifies a 413 bp fragment from wt allele.

Doxycycline-inducible cardiomyocyte-specific overexpression of miRNA-128 (miRNA-128-3p) mice were generated by crossing α-MHC-tTA (The Jackson Laboratory) mice with miRNA-128$^{TetRE}$ mice, in which tetracycline-responsive transcriptional activator (tTA) expression is under the control of α-MHC promoter. Doxycycline (Dox, Harland Laboratories) containing diet was administered to repress transgene expression.

Generation of Mice with a Conditional Deletion of miRNA-128

A construct was engineered for conditional disruption of the miRNA-128 (miRNA-128-3p) gene in which a 1.7 kb fragment spanning the miRNA-128 gene was flanked by two loxP sites. The 1.7 kb fragment, the 5.4 kb left homology arm and the 2.9 kb right homologous arm were amplified from C57BL/6 BAC DNA and cloned into the pBasicLF-NeoFL vector sequentially by in-fusion cloning and confirmed by sequencing. In addition to conditional knockout (cKO) region and homology arms, the targeting construct also contains Frt sites flanked Neomycin cassette for positive selection and a DTA cassette for negative selection. The construct was linearized with NotI and electroporated into C57BL/6N ES cells. After G418 selection, 3 positive clones were identified from 280 G418 resistance clones by PCR screening. The positive clones were expanded and further analyzed by Southern blot. The random integration of extra copies of targeting construct was excluded by hybridization with a neomycin probe. To generate chimeras, ES cell clones were microinjected into blastocysts, and the blastocysts were implanted into pseudo-pregnant foster mice by Cyagen Biosciences Inc. Chimeric males were bred with Flp delete mice from Jackson Laboratories to generate Neomycin-free floxed mice. The correct integration of loxP sites and the successful removal of Neomycin cassette were confirmed by the following PCR assays: 1). Primers 5'-TCATAGCTGTACTTACTGGATG-3' (SEQ ID NO: 8) and 5'-CACTTGGGCTTGGAAGATAG-3' (SEQ ID NO: 9) for the 234 bp fragment from wt allele and the 289 bp fragment from targeted allele. 2). Primers 5'-GCCCTAATTTGATCATCAGAACC-3' (SEQ ID NO: 10) and 5'-CATTGTTGTAGCCACACCCC-3' (SEQ ID NO: 11) for the 483 bp from wt allele and the 605 bp fragment from targeted allele.

Cardiac specific miRNA-128 knockout mice (miRNA-128$^{-/-}$) were generated by crossing Nkx2.5Cre (The Jackson Laboratory) mice with miRNA-128$^{floxP/floxP}$ mice (miRNA-128$^{fl/fl}$)

Tamoxifen (TAM) inducible cardiomyocyte-specific miRNA-128 knockout mice (iKO) were generated by crossing α-MHC$^{MerCreMer}$ mice (Tg(α-MHC-cre/Esr*)1 Jmk/J, The Jackson Laboratory) with miRNA-128$^{fl/fl}$ mice. Induction of Cre recombinase activity was achieved using a two dose of tamoxifen (Sigma, 0.25 mg/g body weight) dissolved in corn oil (Sigma) administrated intraperitoneally (IP). A dual-lineage tracing system was established to investigate the origin of regenerated cardiomyocytes. α-MHC$^{MerCreMer}$ mice were crossed with Rosa26-tdTomato (R26R-mTmG, The Jackson Laboratory) reporter mice and miRNA-128$^{fl/fl}$ mice to generate iKO-mTmG mice (α-MHC$^{MerCreMer}$; miRNA-128$^{fl/+}$; R26R-mTmG) to label miRNA-128 deleting CM with red color following tamoxifen administration. All mice were maintained on a C57BL/6 background.

Neonatal Cardiomyocyte Isolation and Culture

Neonatal rat cardiomyocytes were isolated from ventricles of 1-day-old neonatal Sprague-Dawley rats (Harland) using a neonatal cardiomyocyte isolation kit (Worthington Biochemical) according to the manufacturer's instructions. Neonatal mouse cardiomyocytes were isolated from 1-day-old (P1) C57BL/6 mice with a modified protocol as previously described. The mouse neonatal cardiomyocytes were cultured in 0.1% gelatin plus with 10 μg/ml fibronectin (Sigma-Aldrich) coated slides with 68% DMEM high glucose medium supplemented with 17% M-199, 4% horse serum (Gibco), 10% FBS, and 1% penicillin/streptomycin (hereafter referred to as 'complete-medium') at 37° C. and 5% CO2.

Adult Cardiomyocyte Isolation and Culture

Adult mouse cardiomyocytes were isolated from adult C57BL/6 mice with modified protocol as previously described. The adult mouse CMs were cultured in laminin (10 μg/ml, Life technologies) coated slides with AW medium (Cellutron life technologies) with 10% FBS. After the cells were allowed to adhere for 48 hours in complete-medium, miRNA mimic miRNA inhibitor, siRNA transfection were performed according to the manufacturer's instructions. After 72 hours, cells were harvested for analysis.

Luciferase Reporter Assay

The DNA fragment containing 3'-untranslated regions (3'UTR) was amplified by PCR and cloned into luciferase reporter vector-psiCheck2 (Promega). The reporter vector containing mutant 3'UTR was generated by Site-Directed Mutagenesis Kit (New England Biolabs). HEK-293 cells were transfected using DharmaFECT Duo reagent (Dharmacon) according to the manufacturer's instructions with luciferase reporter vector and miRNA-128 mimic (Dharmacon). Cells were harvested and assayed for luciferase activity using Dual-Glo™ kit (Promega) 48 hours after transfection as previously described.

Quantitative Real-Time PCR (qPCR)

Total RNA was isolated using Trizol reagent (Invitrogen), followed by DNase treatment and purification using RNeasy mini column kit (Qiagen). cDNA was synthesized using miScript PCR Starter Kit (Qiagen) in a 20-μl reaction mixture. qPCR was performed on the CFX96 Real Time PCR system (Bio-Rad) using the protocol of miScript PCR Starter Kit (Qiagen). The fold changes of each target mRNA expression relative to GAPDH under experimental and control conditions were calculated based on the threshold cycle (CT) as r=2−Δ(ΔCT), where ΔCT=CT(target)−CT (GAPDH) and Δ(ΔCT)=ΔCT(experimental)−ΔCT(control). The primers for qPCR include:

```
H3K27me3-p27-F:
                                    (SEQ ID NO: 12)
GAGATCCTACGGTGGAAGCG;

H3K27me3-p27-R:
                                    (SEQ ID NO: 13)
CTTAGCTGGGGTGCGGAATC;

miRNA-128:
                                    (SEQ ID NO: 14)
CGTCACAGTGAACCGGTCTCT;

U6-F:
                                    (SEQ ID NO: 15)
CTCGCTTCGGCAGCACA;

U6-R:
                                    (SEQ ID NO: 16)
AACGCTTCACGAATTTGCGT;

Racgap1-F:
                                    (SEQ ID NO: 17)
CAGATCCAGTGACAATGTTCCA;

Racgap1-R:
                                    (SEQ ID NO: 18)
TCCACCATCATGAACTGATTCC;
```

-continued

Nusap1-F:
GAGGAGGAAGAAGCACAAGAC; (SEQ ID NO: 19)

Nusap1-R:
CTACTATCAGTTCCTTTCATCTCCAA; (SEQ ID NO: 20)

Myh10-F:
GAATTCGAGAGGCAGAACAA; (SEQ ID NO: 21)

Myh10-R:
AAGGCTCGCTTGGATTTCTC; (SEQ ID NO: 22)

Nppa-F:
CTGAGGTGCCTCCCTGGAC; (SEQ ID NO: 23)

Nppa-R:
ACTCTGGGCTCCAATCCTGTC; (SEQ ID NO: 24)

Nppb-F:
AAGGACCAAGGCCTCACAAA; (SEQ ID NO: 25)

Nppb-R:
GCCAGGAGGTCTTCCTACAAC; (SEQ ID NO: 26)

Myh6-F:
GGACGCCCAGATGGCTGACT; (SEQ ID NO: 27)

Myh6-R:
CCTTGTCATCAGGCACGAAGCAC; (SEQ ID NO: 28)

Myh7-F:
GTTTGTCAAGGCCAAGATCGTGT; (SEQ ID NO: 29)

Myh7-R:
AGCATGGCCATGTCCTCGAT. (SEQ ID NO: 30)

Chromatin Immunoprecipitation-qPCR (ChIP-qPCR) Assay

ChIP assay was performed as we described previously to evaluate the enrichment of SUZ12, EZH2, and H3K27me3 on the p27 promoter. SUZ12 (Active Motif), EZH2 (Abcam) and H3K27me3 antibody (Millipore) and normal mouse IgG (Millipore) were used.

Western Blots

Cells were lysed with ice-cold cell lysis buffer plus protease inhibitor (Sigma-Aldrich). Protein samples (40 µg) were mixed and resolved in 4×SDS/PAGE sample buffer and boiled for 15 mins before loading onto 10% polyacrylamide gels (Bio-Rad). The electrophoresed proteins were transferred from the gel to nitrocellulose membranes (Bio-Rad). Equal loading and transfer of proteins was confirmed by quantitative Ponceau red staining. Membranes were incubated for 60 mins with 5% dry milk and Tris-buffered saline to block nonspecific binding sites. Membranes were immunoblotted overnight at 4° C. with antibodies against Cyclin E (Santa Cruz), SUZ12, CDK2, p27 (Cell Signaling Technology) and GAPDH (Sigma-Aldrich) on a rocking platform. After three 5-mins washings with Tris-buffered saline, the membranes were incubated for 60 mins with HRP-conjugated secondary antibody, washed three times with Tris-buffered saline, and finally developed with the ECL plus kit (Thermo Scientific).

Neonatal Mouse Apex Resection

Apex resection (AR) was performed on neonatal mice on postnatal day 1 (P1) as previously described. The hearts were harvested at 6 hours, 24 hours, 3 days, 7 days, 14 days, and 21 days post AR. Sham-operated mouse groups (control) underwent chest opening without apex resection.

Myocardial Infarction (MI) Model

An MI model was developed in female mice, as previously described. Briefly, mice (8-10 weeks old) were anesthetized by spontaneous inhalation and maintained under general anesthesia with 1-2% isoflurane. Animals were mechanically ventilated using a rodent ventilator (Harvard Apparatus) connected to an endotracheal tube. The heart was exposed by a left side limited thoracotomy and the LAD was ligated with a 6-0 polyester suture 1 mm from the apex of the normally positioned left auricle.

Echocardiography

Transthoracic echocardiography (Visual Sonics Vevo 2100) was performed with a 40-MHz probe. Hearts were imaged in 2D long-axis view at the level of the greatest left ventricular (LV) diameter in animals under light general anesthesia. This view was used to position the M-mode cursor perpendicular to the LV anterior and posterior walls. LV end-diastolic (LVDd) and end-systolic diameters (LVDs) were measured from M-mode recordings. LV ejection fraction (EF) was calculated as: EF $\%=[(LVDd)^3-(LVDs)^3/(LVDd)^3 \times 100]$. LV fractional shortening (FS) was determined as: FS $\%=[(LVDd-LVDs)/LVDd \times 100]$. All measurements were performed according to the American Society for Echocardiography leading-edge technique standards, and were averaged over three consecutive cardiac cycles.

EdU Pulse-Chase

For EdU (5-ethynyl-2'-deoxyuridine, Life technology) labeling experiments in vivo, animals were injected intraperitoneally (IP) at 200 ug/g body weight. EdU staining was performed with Click-iT EdU Imaging kit (Thermo Fisher Scientific) according to the manufacturer's instructions.

Analysis of Left Ventricular (LV) Fibrotic Area

Masson's trichrome staining was performed to quantify fibrosis area in the left ventricle post injury. An Olympus BX41 microscope equipped with CCD (Magna-Fire™) camera captured LV area images on each slide. LV fibrosis area and total LV area of each image were measured using the Image J and fibrosis area was reported as a percentage of the total LV area.

Immunohistochemistry Assay

After deparaffinization and microwaving antigen retrieval in citric acid buffer, heart sections were incubated for 1 h at 37° C. or overnight at 4° C. with the following antibodies: Anti-cTnT antibody (Thermo Fisher Scientific) was used to identify CM. Anti-Ki67 (Abcam), anti-EdU (Life technology), anti-phosphorylated-histone 3 (pH3, Millipore) antibodies were used to analyze cell-cycle activity, DNA synthesis, karyokinesis, and cytokinesis respectively. After triple washing in PBS, slides were incubated for 45 mins at 37° C. with fluorescence conjugated second antibodies (Jackson Immuno Research). For wheat germ agglutinin (WGA) staining, slides were incubated for 30 mins at 37° C. with primary antibody against conjugated to Alexa Fluo 488 (Thermo Fisher Scientific) in PBS. To quantify apoptotic CMs, additional mouse hearts were stained with TUNEL (Promega) and cTnT (Thermo Fisher Scientific) according to the manufacturer's instructions. To quantify CM proliferation, cells were stained with Ki67, pH3. DAPI was used for nuclear counterstaining. Four fields of each section were examined for quantification. Fluorescent imaging was performed with an Olympus BX41 microscope equipped with an epifluorescence attachment.

Statistical Analysis

Results were statistically analyzed with the use of the StatView 5.0 software package (Abacus Concepts Inc., Berkeley, Calif.). All values are expressed as mean f S.E.M. Student's-test was applied appropriately for comparison between two treatment groups. One-way ANOVA (using the post-hoc Bonferroni/Dunn test) was performed for comparisons of multiple groups in each of the specific experimental designs presented in the figures.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

---

What is claimed:

1. A method for increasing proliferation of cardiomyocytes in a subject that overexpresses miRNA-128 in the heart, the method comprising delivering a composition to a myocardial region of the subject, the composition comprising:
a therapeutically effective amount of an anti-miRNA-128 oligonucleotide having at least 80% sequence identity with SEQ ID NO: 2; and
a carrier designed for targeted delivery to the myocardial region of the subject, wherein delivering comprises direct injection to the myocardial region of the subject.

2. The method according to claim 1, wherein delivering comprises administering one of the following: a plasmid or vector comprising a genetic construct of the anti-miRNA-128 oligonucleotide, one or more chemically synthesized anti-miRNA-128 oligonucleotides, and combinations thereof.

3. The method of claim 1, wherein the subject suffers from a cardiac disorder selected from the group consisting of ischemic cardiomyopathy, non-ischemic cardiomyopathy, dilated cardiomyopathy, diabetic cardiomyopathy, valvular heart disease, heart failure, myocardial stunning, stroke, hypotension, embolism, thromboembolism, and combinations thereof.

4. The method according to claim 2, wherein the plasmid or vector comprises a DNA vector adapted to express an anti-miRNA-128 oligonucleotide.

5. The method according to claim 2, wherein the plasmid or vector is engineered to transfect the cardiomyocytes with at least one anti-miRNA-128 oligonucleotide.

6. The method according to claim 2, wherein the plasmid or vector is engineered to transfect the cardiomyocytes to block transcription or biogenesis of miRNA-128.

7. The method according to claim 1, wherein the anti-miRNA-128 oligonucleotide is modified by conjugation to one or more of a fatty acid, lipid, saccharide, peptide, protein, locked nucleotide analogue (LNA), and morpholino oligomer.

8. The method according to claim 1, wherein the inhibition is transient.

9. The method according to claim 2, wherein delivering comprises administering a plasmid or viral vector engineered to transfect cardiomyocytes located in the myocardial region with the inhibitor.

10. The method according to claim 1, wherein direct injection is via catheter-based direct intramyocardial injection to a damaged myocardial region of the subject.

* * * * *

UNITED STATES PATENT AND TRADEMARK OFFICE
CERTIFICATE OF CORRECTION

PATENT NO. : 11,365,412 B2
APPLICATION NO. : 16/500481
DATED : June 21, 2022
INVENTOR(S) : Yigang Wang and Wei Huang It is certified that error appears in the above-identified patent and that said Letters Patent is hereby corrected as shown below:

In the Specification

In Column 14, Line 66, delete "Nkx2.3$^{Cre}$" and insert -- *Nkx2.5*$^{Cre}$ --, therefor.

In Column 17, Line 50, delete "Ngpb" and insert -- Nppb --, therefor.

In Column 18, Line 59, delete "ACTCCAAGGCCACTrATCACC" and insert -- ACTCCAAGGCCACTTATCACC --, therefor.

In Column 18, Line 60, delete "ATGTACCAACTGGGACGACA" and insert -- ATTGTTACCAACTGGGACGACA --, therefor.

In Column 19, Line 35, delete "GCCCTAATITGATCATCATCAGAACC" and insert -- GCCCTAATTTGATCATCATCAGAACC --, therefor.

In Column 23, Line 4 & 5, delete "f S.E.M. Student's-test" and insert -- ± S.E.M. Student's *t*-test --, therefor.

Signed and Sealed this
Thirteenth Day of December, 2022

Katherine Kelly Vidal
*Director of the United States Patent and Trademark Office*